United States Patent
Sakamoto et al.

(10) Patent No.: US 7,341,864 B2
(45) Date of Patent: Mar. 11, 2008

(54) MOLECULE TRANSFERRING DEVICE, AUXILIARY FOR MOLECULE TRANSFERRING DEVICE, AND MOLECULE TRANSFERRING METHOD

(75) Inventors: Yoshitaka Sakamoto, Nisshin (JP); Masafumi Koide, Nagoya (JP); Juichiro Nakashima, Nisshin (JP); Susumu Satoh, Osaka (JP); Sousuke Miyoshi, Osaka (JP); Akiko Suzuki, Osaka (JP); Hiroyuki Arakawa, Osaka (JP); Hiroshi Marusawa, Osaka (JP)

(73) Assignees: The Hollenniun Laboratories, Aichi (JP); Meiryo Technica Corporation, Ltd., Aichi (JP)

( * ) Notice: Subject to any disclaimer, the term of this patent is extended or adjusted under 35 U.S.C. 154(b) by 537 days.

(21) Appl. No.: 10/182,262
(22) PCT Filed: Jan. 29, 2001
(86) PCT No.: PCT/JP01/00565
§ 371 (c)(1),
(2), (4) Date: Nov. 13, 2002
(87) PCT Pub. No.: WO01/55294
PCT Pub. Date: Aug. 2, 2001

(65) Prior Publication Data
US 2003/0092182 A1 May 15, 2003

(30) Foreign Application Priority Data
Jan. 27, 2000 (JP) .............................. 2000-023340

(51) Int. Cl.
C12M 1/42 (2006.01)
C12M 3/00 (2006.01)
C12N 13/00 (2006.01)
C12N 15/87 (2006.01)
C12N 15/82 (2006.01)

(52) U.S. Cl. ................ 435/285.2; 435/461; 435/173.6; 435/2; 435/470

(58) Field of Classification Search ................ 435/461, 435/173.6, 285.2, 470; 601/2
See application file for complete search history.

(56) References Cited

U.S. PATENT DOCUMENTS
4,822,470 A * 4/1989 Chang ........................ 435/450

(Continued)

FOREIGN PATENT DOCUMENTS
| JP | 04-252173 A | 8/1992 |
| JP | 11-206372 A | 8/1999 |
| JP | 11-290058 A | 10/1999 |
| WO | WO 89/03426 A | 4/1989 |

OTHER PUBLICATIONS
European Search Report (Dated May 14, 2003).

*Primary Examiner*—Gladys J P Corcoran
*Assistant Examiner*—Nathan Bowers
(74) *Attorney, Agent, or Firm*—Donald R. Studebaker; Nixon Peabody, LLP

(57) ABSTRACT

A molecule introducing apparatus is provided with a power supply circuit 20 for supplying power, a step-up transformer 30 which is supplied with power from the power supply circuit 20 and which outputs a high voltage, a switching transistor 22 that blocks off and allows the supply of power from the power supply circuit 20 to the step-up transformer 30 and which generates an instantaneous high voltage, and a pair of electrode probes 50 for applying the instantaneous high voltage generated at the step-up transformer 30 to a predetermined region in a body. The molecule introducing apparatus oscillates DNA arranged outside a cell by the instantaneous high voltage so as to introduce the DNA into the cell.

11 Claims, 14 Drawing Sheets
(1 of 14 Drawing Sheet(s) Filed in Color)

U.S. PATENT DOCUMENTS

| | | |
|---|---|---|
| 4,846,178 A | 7/1989 | Fuxue et al. |
| 4,970,154 A * | 11/1990 | Chang ..................... 424/93.21 |
| 5,098,843 A | 3/1992 | Calvin |
| 5,283,194 A | 2/1994 | Schmukler |
| 5,318,514 A | 6/1994 | Hofmann |
| 5,422,272 A * | 6/1995 | Papp et al. .............. 435/285.2 |
| 5,506,765 A * | 4/1996 | Nakata et al. ................. 363/98 |
| 5,694,311 A * | 12/1997 | Umeda et al. ................. 363/89 |
| 5,753,477 A | 5/1998 | Chan |
| 5,869,326 A * | 2/1999 | Hofmann ................. 435/285.2 |
| 5,983,131 A * | 11/1999 | Weaver et al. ................ 604/20 |
| 5,993,434 A * | 11/1999 | Dev et al. ................... 604/501 |
| 6,040,184 A * | 3/2000 | Greener et al. ............. 435/461 |
| 6,056,861 A * | 5/2000 | Fuhr et al. ................. 204/547 |
| 6,135,990 A * | 10/2000 | Heller et al. ................ 604/500 |
| 6,344,349 B1 * | 2/2002 | Moldavsky et al. ..... 435/173.5 |
| 2006/0024359 A1* | 2/2006 | Walker et al. .............. 424/450 |

* cited by examiner

MOLECULE TRANSFERRING DEVICE, AUXILIARY FOR MOLECULE TRANSFERRING DEVICE, AND MOLECULE TRANSFERRING METHOD

The patent or application file contains at least one drawing executed in color. Copies of this patent or patent application publication with color drawings will be provided by the office upon request and payment of the necessary fee.

TECHNICAL FIELD

The present invention relates to a molecule introducing apparatus for introducing molecules such as DNA into a cell, an auxiliary tool for the molecule introducing apparatus, and a molecule introducing method, for application in fields including medicine and biology.

BACKGROUND ART

Gene therapy has received considerable attention in recent years. However, a method for reliably introducing genes into organisms has yet to be established. At present, DNA is introduced through the liposome method, the virus method, the calcium phosphate method, direct introduction via gene gun or the like, and electroporation. Electrical methods employ either a rectangular DC pulse or an exponentially attenuating pulse.

A molecule introducing apparatus that adopts electroporation has been disclosed in JP-2739978B. With this molecule introducing apparatus, a plurality of organism particles are arranged between electrodes in a solution and a pulsed high-frequency oscillation field is applied between the electrodes to carry out poration and permeation of the organism particles.

PROBLEMS TO BE SOLVED

Introducing DNA through the above-mentioned conventional techniques of the liposome method, the virus method, the calcium phosphate method, direct introduction via gene gun, or electroporation proved problematic because none achieved a safe and secure introduction of DNA into an organism.

Electrical methods use a rectangular DC pulse or an exponentially attenuating pulse, and therefore cause unavoidable damage to tissue and cells when DNA is introduced. Moreover, it is difficult to reliably introduce DNA into the entire target cell or tissue with these electrical methods.

The molecule introducing apparatus disclosed in JP-2739978B employs a method for conducting an RF high frequency current pulse through a solution. In this case, the increase in current (number of electrons) flowing through the solution damages the cells. The conducted power must be lowered in order to prevent damage to the cells. However, lowering the conducted power causes a drop in the ability of cells to oscillate, for example. The outcome was that molecules could not be reliably introduced into cells.

The present invention was arrived at in light of the foregoing problems, and it is an object thereof to reliably introduce molecules such as DNA into an organism body, cultured tissue, adherent cells, or floating cells of an animal, plant or other organism without causing damage, so as to bring about the expression of proteins or activation.

DISCLOSURE OF THE INVENTION

The present invention is an apparatus that imparts a larger kinetic energy to molecules that are to be introduced into a cell than the intermolecular bonding energies. As a result, the molecules can be safely introduced into cells without forming a pore or the like in the cell.

Years of focused research into how to impart a large kinetic energy to a molecule has lead the inventors to the following findings. According to the present invention, an electric, magnetic, or acoustic field targeting in vivo tissue or cells is formed. This is followed by the excitation of molecular resonance motion and the repeated depolarization of the cell membrane by reversibly switching its polarization, which together enable the transmission of molecules inside and outside the cell through the cell membrane. That is, if a cell membrane with an electrically negative charge is reversed in polarization to a positive charge, then the mutually repelling force between it and molecules that are also negatively charged is eliminated and they become attracted to one another. The result is the movement of molecules such as DNA into the cell.

To explain this in greater detail, the electrical discharge in the present invention is for example a single spike only, where the high point and low point of the spike lead to only an initial first vibration. All subsequent vibrations are resultant of the phenomenon of a reverberation reaction in the resonance circuit that includes the biological system. Consequently, all the vibration reactions are secondary phenomena accompanying a single excitation, and the output of an oscillatory wave (high frequency wave) is not necessarily required.

The system by which molecules for introduction move into a cell is as follows. Irrespective of the type of instantaneous excitation of high voltage, every kind of molecule has its own self-oscillation properties, which are defined by its molecular weight, electrical charge characteristics, charged sites, and spatial structure, among others. This results in phase variation in the resonance oscillation of the molecules and variation in the attenuation of the relative kinetic moment of the molecules. At times, the phenomenon of molecules repelling one another and colliding with one another may occur. Consequently, there is repeated collision and repellence between the molecules to be introduced and the molecules constituting the cell membrane, and in the instant the spatial structure of the cell membrane is warped, for example, the molecules are afforded an opportunity to infiltrate into the cell.

The electrical attenuating oscillation that accompanies this instantaneous stimulus can be observed as the total resonance motion of the introduction apparatus and the electrons and molecules included in the biological circuit, and reflects the event of molecules infiltrating into the cell.

The present invention is equivalent to obtaining an oscillation at a liquid surface by dropping a pebble into still water, whereas a high frequency method is equivalent to oscillating the surface of a liquid by an oaring motion. Dropping a stone leads to an oscillation pattern appropriate for the volume and physical properties of the liquid itself, be it oil, water, or some other liquid. In contrast, the motion of oaring the liquid in itself applies an unsuitable vibration at the liquid surface, so that a large oscillation cannot be obtained. To achieve oscillations with equal amplitudes, dropping a pebble clearly results in less energy loss than an oaring motion. For example, in the case of sound, the method of the present invention is like obtaining a resonance sound by striking a tuning fork, whereas a high frequency stimulus is equivalent to finely shaking the tuning fork. Clearly, striking the tuning fork obtains a cleaner resonance.

Accordingly, an instantaneous high voltage is employed in an embodiment of the present invention.

To provide a more specific description, the first through seventeenth aspects of the invention relate to a molecule introducing apparatus. According to a first aspect of the invention, an electrical field, a magnetic field, or an acoustic field is formed by applying voltage directed at a biological tissue or cell and enable molecules to pass through a membrane into the cell.

According to a second aspect of the invention, an electrical field, a magnetic field, or an acoustic field is formed by an instantaneous high voltage directed at a biological tissue or a cell to excite a free resonance circuit that includes the biological tissue or the cell and cause reverberation between molecules constituting the cell and the molecules to be introduced, so as to introduce the molecules into the cell.

According to a third aspect of the invention, the apparatus is provided with a voltage generating means for generating voltage and a high impedance voltage applying means for receiving voltage generated by the voltage generating means and creating an electric field at a predetermined region in a body so as to introduce molecules arranged outside a biological tissue or a cell into cells.

According to a fourth aspect of the invention, in the third aspect of the invention, the voltage applying means forms a portion of a free resonance circuit including the predetermined region in the body.

According to a fifth aspect of the invention, in the third aspect of the invention, the voltage applying means is configured so that its electrodes generate an electric field around biological tissues or cells in the body via a high insulation portion.

According to a sixth aspect of the invention, in the third aspect of the invention, the voltage generating means is provided with a power supply means for supplying power, a voltage step-up means that is supplied with power from the power supply means and that supplies high voltage to the voltage applying means, a switching means, which blocks/allows the supply of power from the power supply means to the voltage step-up means and causes the voltage step-up means to generate the voltage to be supplied to the voltage applying means, and a switching control means for controlling the switching of the switching means.

According to a seventh aspect of the invention, in the sixth aspect of the invention, the power supply means is provided with a power source and a power adjustment circuit for receiving power from the power source and outputting a control power.

An eighth aspect of the invention is a molecule introducing apparatus, wherein in the seventh aspect of the invention, the power adjustment circuit is configured so that it supplies a predetermined power to the voltage step-up means and the switching control means, and fixedly or changeably controls the voltage and the current to be supplied.

According to a ninth aspect of the invention, in the sixth aspect of the invention, the voltage step-up means is provided with a low voltage portion that drives depending on the switching means and a high voltage portion that constitutes a portion of the voltage applying means, and the voltage step-up means is configured to step up voltage to a predetermined voltage based on a preset step-up ratio between the low voltage portion and the high voltage portion.

According to a tenth aspect of the invention, in the sixth aspect of the invention, the switching control means is configured so that it outputs a control signal with a variable frequency in order to control the driving of the switching means.

According to an eleventh aspect of the invention, in the sixth aspect of the invention, the switching means is configured so that it blocks/allows the supply of power to the voltage step-up means based on a control signal of the switching control means.

According to a twelfth aspect of the invention, in the sixth aspect of the invention, the voltage applying means is provided with a plurality of electrodes and high insulation portions, and is configured such that the electrodes generate an electric field around biological tissue or cells in the body via the high insulation portions.

According to a thirteenth aspect of the invention, in the sixth aspect of the invention, the voltage step-up means is a transformer or a piezoelectric element that generates a high voltage based on piezoelectric effects.

According to a fourteenth aspect of the invention, in the third aspect of the invention, the voltage applying means has a variable capacitance structure or a variable reactance structure in which resonance properties due to the distributed capacity can be actively changed.

According to a fifteenth aspect of the invention, in the third aspect of the invention, the voltage applying means is provided with a spark gap or a discharge tube in series or in parallel with the voltage step-up means.

According to a sixteenth aspect of the invention, in the fifth or twelfth aspects of the invention, the high insulation portion of the voltage applying means is a high insulation shield arranged in close proximity to the electrodes or is a high insulation jacket that covers the electrodes.

According to a seventeenth aspect of the invention, in the fifth or twelfth aspects of the invention, the electrodes are made of a conducting substance that includes metal, ceramic, or an organic substance.

According to an eighteenth aspect of the invention, in the twelfth aspect of the invention, the switching control means is configured such that it can output single-phase alternating current waveforms, three-phase alternating current waveforms, multiphase alternating current waveforms, and a plurality of frequencies or synthesized waveforms. Also, the voltage step-up means is configured such that it can output a positive voltage burst, a negative voltage burst, and voltage combining the two bursts. Moreover, there is a plurality of the voltage step-up means, which are configured so as to generate a potential difference between the plurality of electrodes.

On the other hand, the nineteenth aspect through the thirtieth aspect of the invention relate to molecule introducing methods. According to the nineteenth aspect of the invention, an electrical field, a magnetic field, or an acoustic field is formed by applying voltage directed at a biological tissue or cell, after which molecules are passed through a membrane into the cell.

According to a twentieth aspect of the invention, an electrical field, a magnetic field, or an acoustic field is formed by an instantaneous high voltage directed at a biological tissue or cell so as to excite a free resonance circuit that includes the biological tissue or the cell, cause reverberation between molecules constituting the cell and molecules to be introduced, and introduce the molecules into the cell.

According to a twenty-first aspect of the invention, molecules to be introduced into a cell are distributed around a biological tissue or a cell before a high voltage is repeatedly applied around the biological tissue or the cell so as to introduce the molecules into the cell in a micro-current high-voltage environment.

According to a twenty-second aspect of the invention, molecules to be introduced into a cell are distributed around a biological tissue or a cell, after which a high voltage is repeatedly applied around the biological tissue or the cell so as to form, in a micro-current high-voltage environment, a free resonance circuit including a predetermined region of the biological tissue or the cell and introduce the molecules into the cell.

According to a twenty-third aspect of the invention, molecules to be introduced into a cell are distributed around a biological tissue or a cell, after which a high voltage from electrodes is repeatedly applied around the biological tissue or the cell via a high insulation portion so as to form, in a micro-current high-voltage environment, a free resonance circuit including a predetermined region of the biological tissue or the cell and introduce the molecules into the cell.

According to a twenty-fourth aspect of the invention, in either the twenty-second or the twenty-third aspects of the invention, the micro-current high-voltage environment is made by a molecule introducing apparatus that is provided with a power supply means for supplying power, a voltage step-up means that is supplied with power from the power supply means and generates a high voltage, a switching means, which blocks/allows the supply of power from the power supply means to the voltage step-up means and generates a high voltage in the voltage step-up means, a switching control means for controlling the switching of the switching means, and a voltage applying means for receiving the high voltage generated by the voltage step-up means and creating an electric field at a predetermined region in a body so as to introduce molecules arranged outside a biological tissue or a cell into cells.

According to a twenty-fifth aspect of the invention, in any one of the nineteenth through twenty-third aspects of the invention, the molecules are polynucleotides, proteins, viruses, low molecule compounds including various drugs, or cell molecules.

According to a twenty-sixth aspect of the invention, in any one of the nineteenth through twenty-third aspects of the invention, the biological tissue is animal or plant tissue, and the cell is an animal, plant or microbe cell or a cell cloned from an animal, plant or microbe.

According to a twenty-seventh aspect of the invention, in the twenty-fourth aspect of the invention, the passage of molecules through the membrane is adjusted by varying the application voltage that is administered, the resonance constant, or the positions of the electrodes.

According to a twenty-eighth aspect of the invention, in any one of the nineteenth through twenty-third aspects of the invention, the molecule are prepared in a solution containing at least one of saponin, digitonin, a surfactant such as dimethyl sulfoxide, ionophores, lipids, ceramide, albumin, glycerin, gelatin, and serum, or molecules for controlling the osmotic pressure or the ion balance inside and outside the cell membrane.

According to a twenty-ninth aspect of the invention, in any one of the nineteenth through twenty-third aspects of the invention, the molecules have been developed into an ointment, cream, gel substrate, or aqueous solution for injection, and are administered to a body surface, adhered to a body surface, or injected into the body.

According to a thirtieth aspect of the invention, in any one of the nineteenth through twenty-third aspects of the invention, the molecules are developed into a cell culture solution or polyethylene glycol and are passed through the membrane into the cell.

Also, a thirty-first and a thirty-second aspect of the invention relate to an auxiliary tool for the molecule introducing apparatus. According to the thirty-first aspect of the invention, it is provided with a vessel body having predetermined dielectric properties and an indented portion which is formed in at least a portion of the vessel body and which concentrates an electric field.

According to the thirty-second aspect of the invention, it is an auxiliary tool that is arranged at a predetermined region of an organism, and in which a conducting portion is formed, which concentrates an electric field onto a predetermined region in the organism body.

In other words, it is generally desired that a molecule introducing apparatus, and in particular a DNA introducing apparatus adopting an electrical introduction method, does not harm the target tissue or cell. If a DNA introducing apparatus causes damage to the cells or the tissue, the suitability of the apparatus itself is compromised. Often, the reason why cells are damaged is that too much power is supplied to the target cell. Consequently, it is essential that the DNA introducing apparatus avoids damaging the cells by quickly neutralizing saturation storage electric power before the cells are damaged.

One method for avoiding this is as follows. First, the desired DNA is introduced to predetermined regions in the organism in advance by injection, for example. Then, with a high voltage power source with high impedance, voltage that has been sufficiently stepped up is intermittently applied to the predetermined regions repeatedly.

That is, single pulses of instantaneous high voltage are generated intermittently. By applying this instantaneous high voltage, an electrical free resonance circuit formed by the apparatus itself and the organism is excited, and the charged molecules and electrons constituting this resonance circuit generate an attenuating oscillation.

More particularly, with the present invention the electrodes are arranged in a state of non-contact with the biological tissue and cells and external molecules such as DNA via a high insulation object. Put differently, it is safe to insert the electrodes, which are covered by a high insulation portion, into the biological tissue or cells because no current flows. Then, voltage is applied to the molecules or the like between the electrodes.

At this time, surrounding cells, tissue and the introduced DNA are also incorporated into the free resonance circuit of the surrounding cells and exhibit resonance properties intrinsic to each molecule and oscillate in a freely attenuating oscillation. That is, the DNA distributed near the cell membrane is subject to based on Faraday's laws a dynamic moment in the direction against the reverse electric field when the applied instantaneous electric field is identical to its own charge, and in the forward direction of the electric field in the next instant when the opposite electric field is applied. Due to the continuous motion of the DNA due to the freely attenuating oscillation and the repeated reversible switch in polarity of the cell membrane, an accelerating relative motion occurs between the DNA and the molecules of the cell membrane, and the DNA is allowed to pass through the membrane.

As a result, there is a marked increase in the likelihood of introducing DNA into the cells as compared with the conventional method of applying only direct current to a solution between the electrodes, and damage to the target site and surrounding cells can be reliably prevented.

Depending on the structure of the cell membrane or the cell wall, and taking into account its thickness, a tunnel effect of electrons tunneling through an electron barrier between thin membranes may also be exhibited from voltage applied to the cell membrane or cell wall.

Also, due to a popping phenomenon, in which electron resonance interaction in a high electric field environment excites the surrounding molecules in an accelerating manner, the molecules to be introduced are able to pass through the cell membrane or the cell wall in an avalanche-like fashion.

Particularly in the latter case, a direct current pulse was conventionally supplied in solution to introduce the DNA while electric current flows. With the present invention, a high voltage field is generated, but because a high-impedance high voltage power source and high insulation electrodes are used, almost no current flows through the biological tissue or cells into which the DNA is to be introduced, and thus safety is ensured.

Also, by forming a magnetic field, it is possible to deviate the current, cause electron spin, and control the resonance of molecules such as DNA.

Also, forming an even stronger magnetic field loosens the double helix structure of the DNA and makes it possible to introduce molecules such as DNA into the cell. This also enables the incorporation of molecules such as DNA into the genome.

There is not limitation to free resonance, and it is also possible to impart oscillations with various frequency properties, such as in Fourier waveform synthesis. This makes it possible to cause the resonance of a variety of tissues and cells.

Also, by changing the resistance value or the shape and size of the electrode, appropriate resonance conditions may be observed while the introduction of the molecule is promoted.

EFFECT OF THE INVENTION

According to the present invention, there is a marked increase in the likelihood of introducing DNA into the cells compared with the conventional method of applying only direct current, and damage to the target site and surrounding cells can be reliably prevented.

In particular, the invention can find wide ranging application because the electrodes and the molecules or the like are in a state of non-contact.

Also, according to the seventh aspect of the invention, a power adjustment circuit is provided, so that an instantaneous voltage, for example, suitable for the molecules or the like to be introduced can be created. As a result, molecules can be reliably passed through the membrane.

According to the eighth aspect of the invention, the power adjustment circuit controls the current and the voltage, so that an instantaneous voltage, for example, suitable for the molecules or the like to be introduced can be more precisely generated.

According to the tenth aspect of the invention, the switching control means outputs a control signal of a variable frequency, so that the signal can be adjusted to a period of voltage application that corresponds to the molecules or the like to be introduced.

According to the fourteenth aspect of the invention, the voltage application means is given a variable capacitance structure or a variable reactance structure, so that a resonance circuit corresponding to the molecules or the like to be introduced can be created.

According to a fifteenth aspect of the invention, the voltage applying means is provided with a spark gap or a discharge tube, so that a stable instantaneous voltage or the like can be created.

According to the sixteenth aspect of the invention, different potential differences can be generated between three or more electrodes, so that an instantaneous voltage or the like that matches various kinds of molecules for introduction can be created.

According to the thirty-first and thirty-second aspects of the invention, an electric field vector can be concentrated in a predetermined location, so that the introduction of molecules can be carried out more reliably.

BRIEF DESCRIPTION OF THE DRAWINGS

The patent or application file contains at least one drawing executed in color. Copies of this patent or patent application publication with color drawings will be provided by the office upon request and payment of the necessary fee.

BEST MODE FOR CARRYING OUT THE INVENTION

Hereinafter, embodiments of the present invention will be described in detail with reference to the drawings.

First Embodiment

Figure 1:
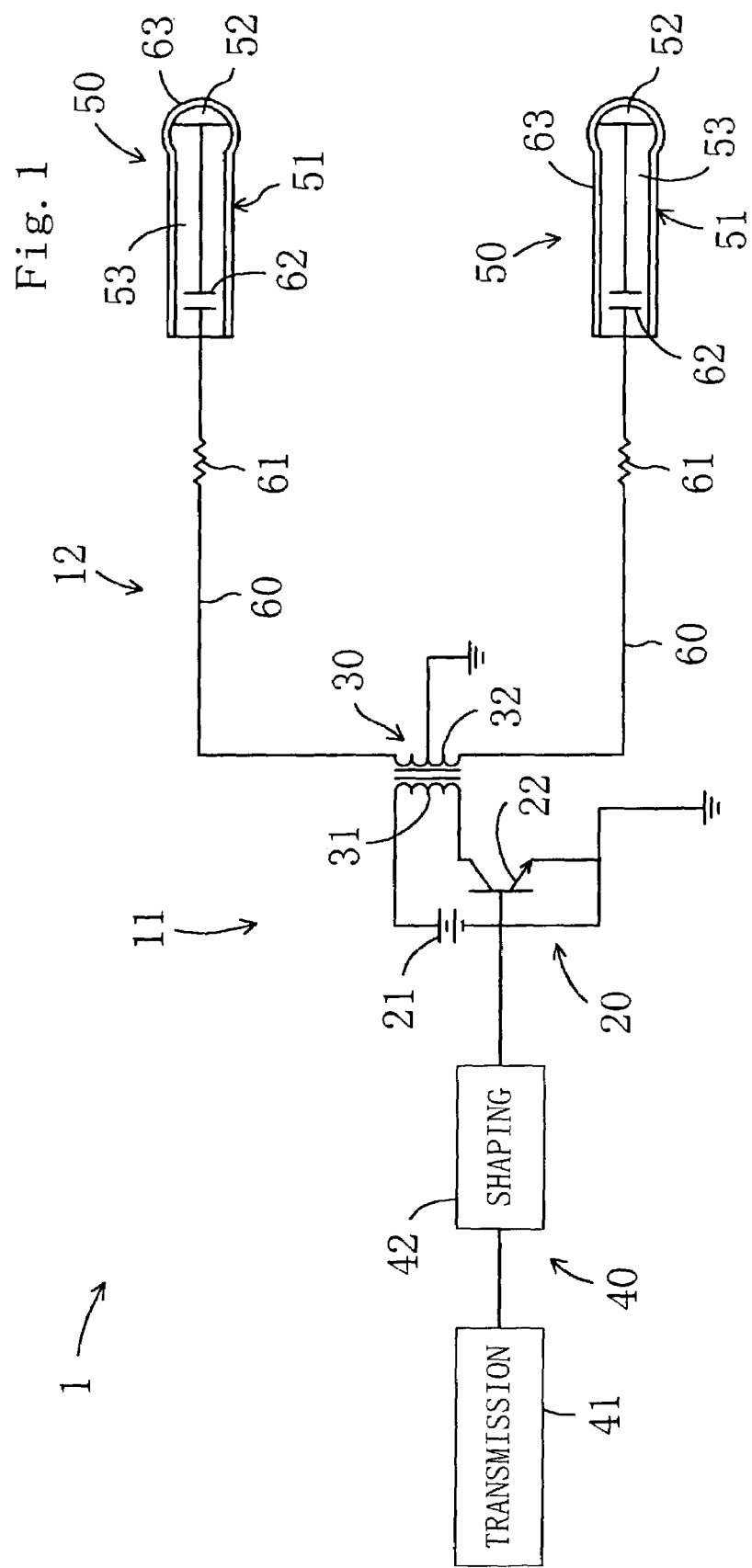
FIG. 1 is an electrical circuit diagram showing the molecule introducing apparatus.
Figure 2:
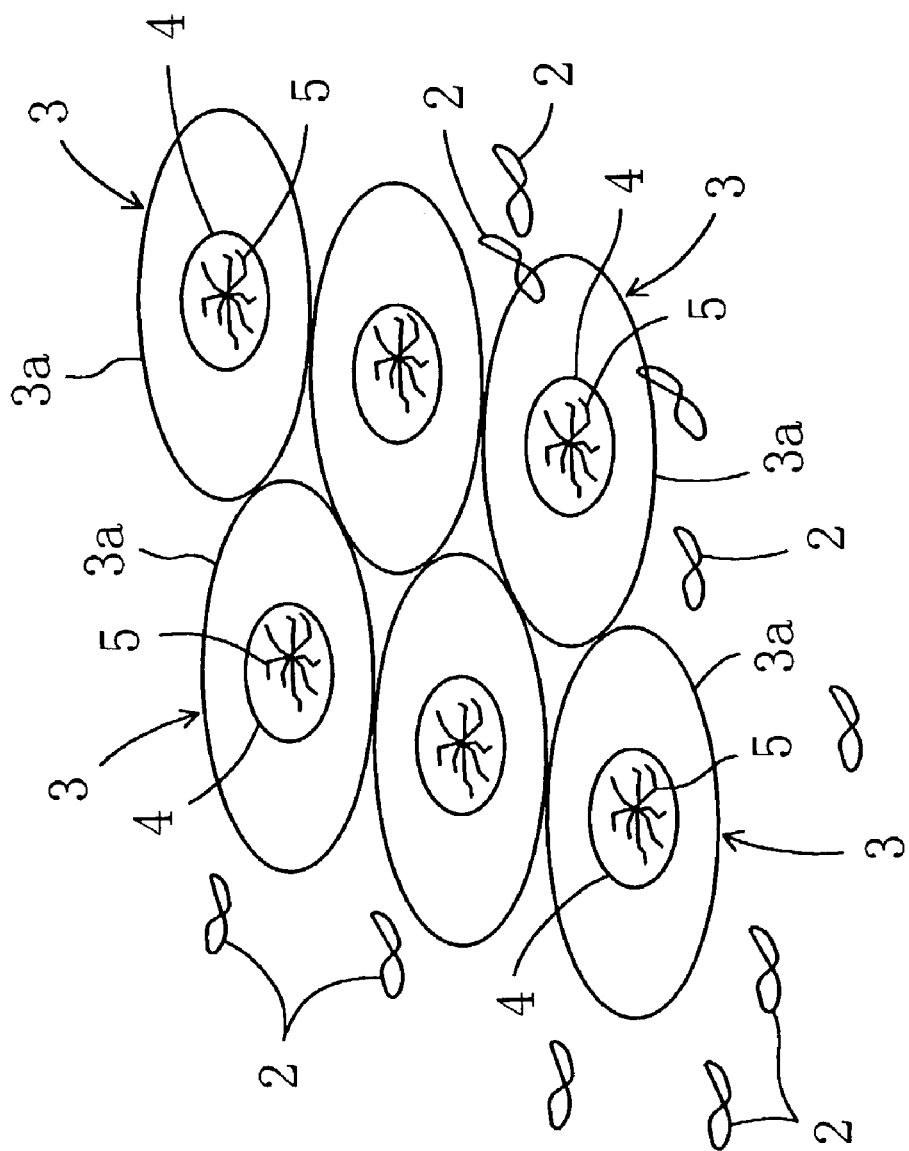
FIG. 2 is a situational diagram that schematically illustrates the passage of DNA through a cell membrane.

As shown in FIG. 1, a molecule introducing apparatus 1 of the present embodiment is a DNA introducing apparatus for introducing DNA molecules into cells in vivo, and is provided with a voltage generating means 11 and a voltage applying means 12. As shown in FIG. 2, a precondition of the molecule introducing apparatus 1 is that a DNA 2 to be introduced has been made to exist in the organism by a means of injection, for example.

Ordinarily, simply injecting the DNA 2 into an organism, the DNA 2 is prevented from infiltrating into a cell 3 by a cell membrane 3a of the cell 3. Consequently, the injected DNA 2 cannot move into the cell 3 and a cell nucleus 4. The result is that changes that are anticipated by injecting DNA 2 do not become manifest.

The voltage generating means 11 is provided with a power supply circuit 20, which is a power supply means, a step-up transformer 30, which is the voltage step-up means and a transformer, a switching transistor 22, which is a switching means, and a signal control circuit 40, which is a switching control means.

The power supply circuit 20 is provided with a direct current power source 21, both ends of which are connected to both ends of a primary winding 31 of the step-up transformer 30. The power supply circuit 20 is configured such that it supplies a constant DC power from the power source 21 to the step-up transformer 30.

The switching transistor 22 is configured such that it supplies and blocks power from the power supply circuit 20 to the primary winding 31 of the step-up transformer 30. That is, the switching transistor 22 both blocks and allows the supply of power to the step-up transformer 30. The switching transistor 22 is connected between the minus side of the power source 21 and the primary winding 31 of the step-up transformer 30, with its collector connected to the primary winding 31 of the transformer 30 and its emitter connected to the ground.

The signal control circuit 40 is provided with a frequency generation circuit 41 and a waveform shaping circuit 42. The frequency generation circuit 41 is configured such that it outputs a control signal of a predetermined frequency set in advance. The waveform shaping circuit 42 is configured such that it shapes the control signal of the frequency generation circuit 41 to a predetermined waveform and outputs the control signal. Also, the waveform shaping circuit 42 is connected to the base of the switching transistor 22 and configured such that it turns the switching transistor 22 on and off with a predetermined timing.

The step-up transformer 30 is provided with the low voltage portion primary winding 31 and a high voltage portion secondary winding 32. Also, the step-up transformer 30 is made to generate a predetermined high voltage at the secondary winding 32 based on a step-up ratio that is determined by the winding ratio of the primary winding 31 to the secondary winding 32.

Figure 3:
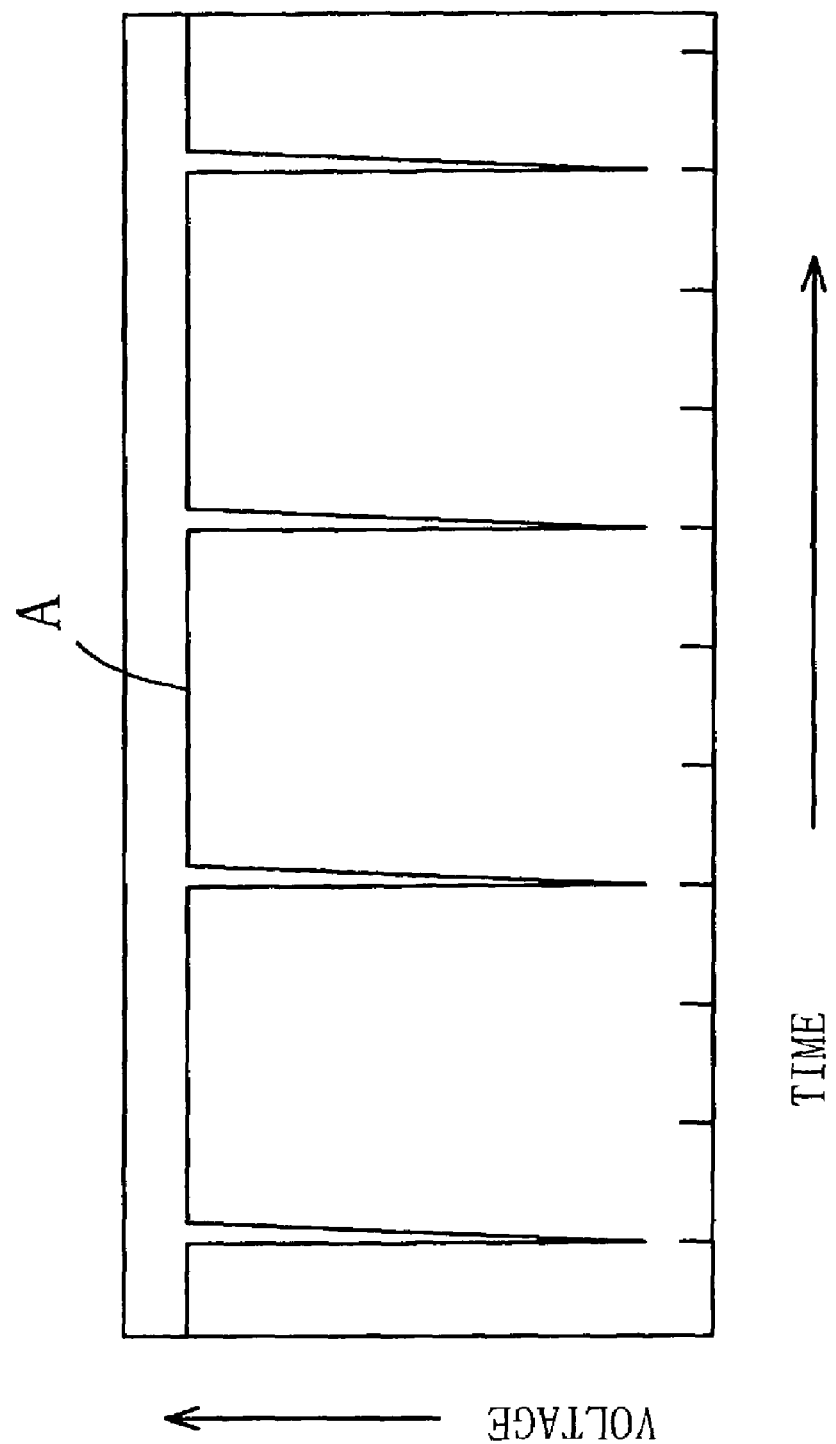
FIG. 3 is a waveform diagram showing the excitation waveform of the step-up transformer.
Figure 4:
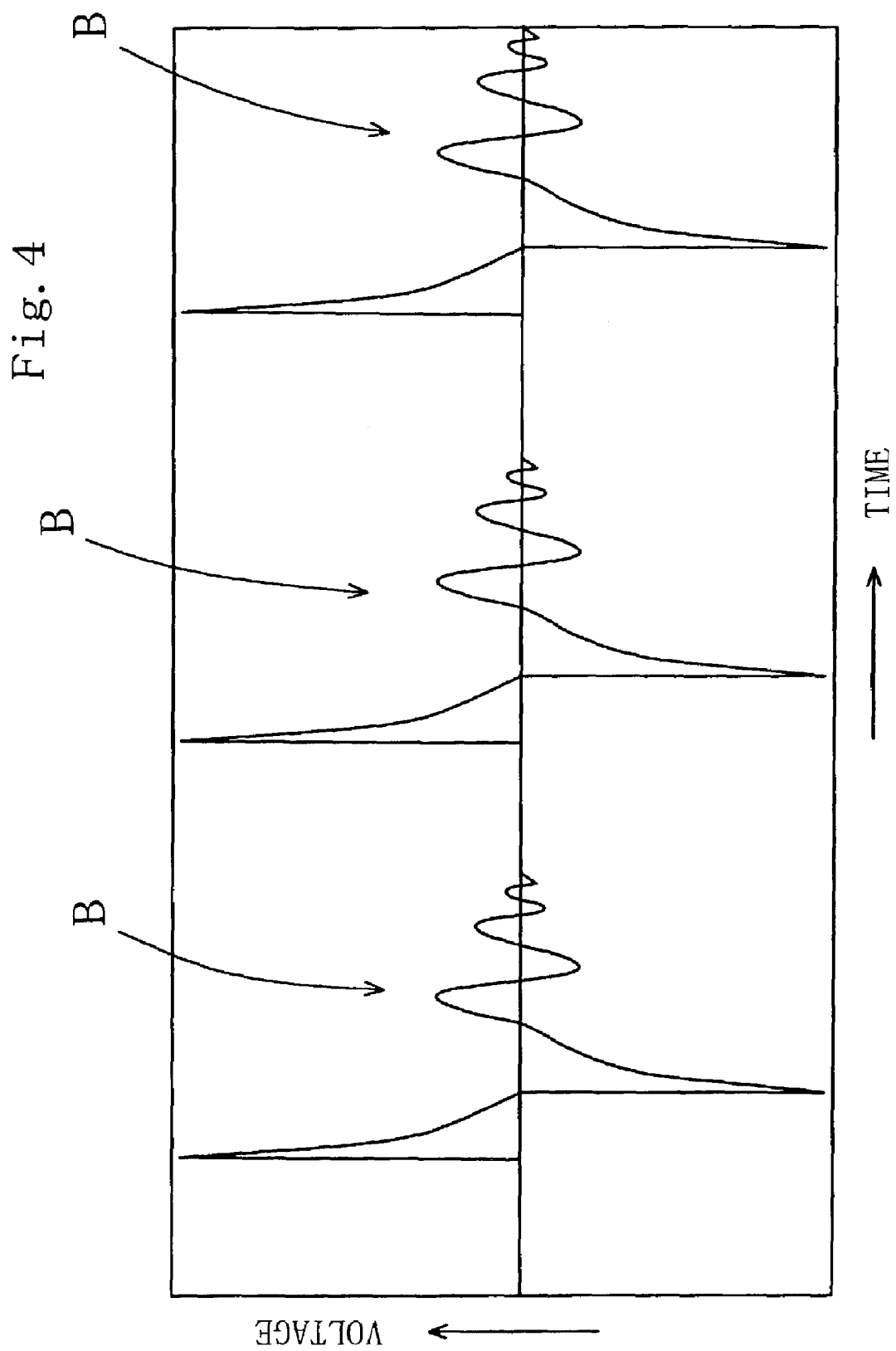
FIG. 4 is a waveform diagram of the instantaneous voltage and the attenuating voltage generated in the secondary winding of the step-up transformer.

As shown in FIG. 3, when the switching transistor 22 is in the on state, the primary winding 31 is excited and the step-up transformer 30 accumulates a predetermined electrical energy A in the primary winding 31, and when the switching transistor 22 is turned off, the step-up transformer 30 releases the accumulated electrical energy. Also, as shown in FIG. 4, electron vibration is induced in the secondary winding 32 of the step-up transformer 30 via fluctuations in the electric field, and thereby induces instantaneous voltage and an alternating voltage B in an attenuating oscillation wave residual from the raw amplitude.

That is, the generation of an instantaneous high voltage in a single pulse induces an alternating voltage B in a sinusoidally attenuating wave.

The voltage applying means 12 is provided with a pair of electrode probes 50, 50 each connected to an end of the secondary winding 32 of the step-up transformer 30 through wires 60, 60. A current limiting resistor 61 for limiting over-currents and a capacitor 62 are connected in series to each wire 60.

The electrode probes 50 are provided with a cylindrical electrode tube 51 and an end electrode 52 accommodated within the electrode tube 51 and connected to the wire 60. Packing material 53, which is an insulating material such as silicon, is packed into the electrode tube 51. Moreover, the electrode probes 50 are provided with a high insulation jacket 63. That is, the electrode tubes 51 are covered by a high insulation jacket 63 having high insulation properties. Because the electrode probes 50 are covered by the high insulation jacket 63, they function as equivalent capacitors that are configured according to the dielectric constant.

The pair of electrode probes 50, 50 are placed at a predetermined region of the organism, or in other words, are arranged in a state of non-contact with predetermined cells 3. The pair of electrode probes 50, 50 are configured such that an instantaneous high voltage is applied near the predetermined cells 3. The voltage applying means 12 constitutes an external resonance circuit that includes the organism, and when the pair of electrode probes 50, 50 come into contact with and carry electricity through the organism tissue, it acts as a differentiator with respect to the external resonance circuit including the organism and supplies a large trigger voltage across the external resonance circuit.

Method for Introducing the DNA 2

Next, the method for introducing the DNA 2 using the above-mentioned molecule introducing apparatus is described.

First, the DNA 2 to be introduced is inserted into the organism in advance by means of injection or the like. Then, the pair of electrode probes 50, 50 are fixed with respect to the organism so as to target the cells 3 into which the DNA 2 is to be introduced. This is followed by supplying direct current power from the power source 21 to the primary winding 31 of the step-up transformer 30, while on the other hand outputting a predetermined control signal from the frequency generation circuit 41. The waveform of this control signal is shaped by the waveform shaping circuit 42 and the signal is output to the base of the switching transistor 22 as a predetermined control signal.

When the switching transistor 22 is turned on by the control signal, a predetermined electrical energy is accumulated in the primary winding 31 of the step-up transformer 30 (see FIG. 3). Then, when the switching transistor 22 is turned off by the control signal, the electrical energy accumulated in the primary winding 31 is released. As shown in FIG. 4, at this time a high-voltage spike and an excitation voltage B accompanying the attenuating oscillation wave are induced in the secondary winding 32 of the step-up transformer 30.

Figure 5:
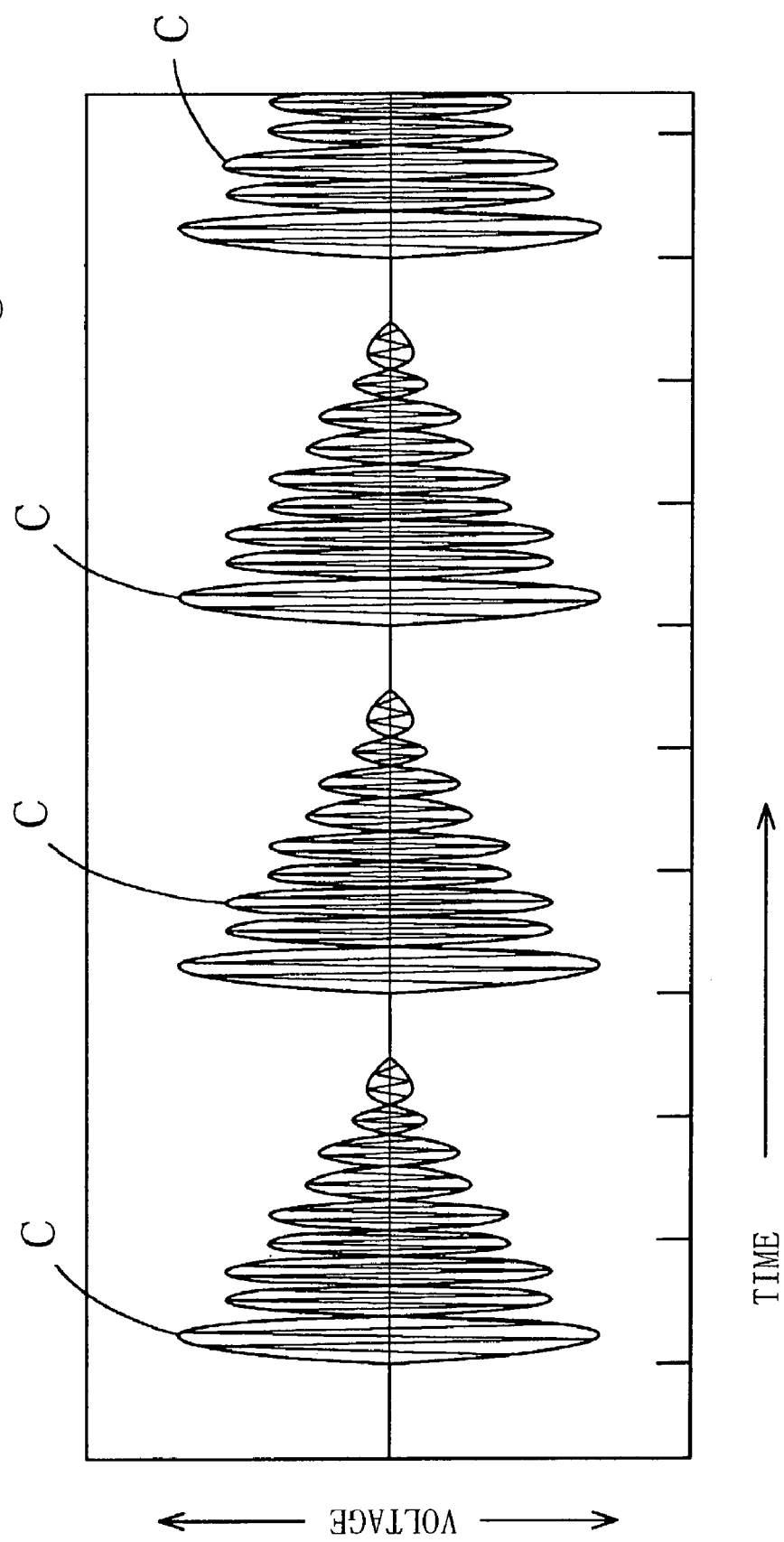
FIG. 5 is a voltage waveform diagram showing the resonance of a cell.

The spike of high voltage acts between the pair of electrode probes 50, 50 so that the voltage applying means 12 forms an external resonance circuit that includes the organism. This instantaneous voltage serves as a trigger voltage and excites the external resonance circuit, which includes the organism, to resonate. Then, as shown in FIG. 5, when the cell 3 is resonated, a voltage fluctuation C having an amplitude modulated waveform formed by the sum of the electrons following the trigger voltage and the resonance action of the charged molecules is observed.

Stimulating the organism by this output voltage causes the biological circuit about the point of voltage application to form an electrical free resonance circuit and induce a sinusoidally attenuating oscillation. The surrounding cells 3 and the DNA 2 are incorporated in the free resonance circuit, which vibrates in synchronization with their self-resonance properties.

The result, as shown in FIG. 2, is that DNA 2 near the cell membrane 3a moves to the opposite electric field side when the electric field that is applied is identical to its own charge, and moves to the electric field side to be neutralized when the electric field that is applied is opposite its own. Then, as a result of continuous motion due to its self-resonance properties and the repeated reversible inversion of the cell membrane 3a, the DNA 2 behavior accelerates. As a result, the DNA 2 passes through the cell membrane 3a and disperses upon colliding with molecules within the cell 3 to become a part of nucleic DNA 5 in the cell nucleus 4. Thus, the desired effect is exhibited.

That is to say, it is generally expected that the molecule introducing apparatus 1, and in particular a DNA introducing apparatus that adopts a method for electrical introduction, does not harm the target in vivo tissue or cells 3. If a DNA introducing apparatus tends to destroy the cells 3 or in vivo tissue, the suitability of the apparatus itself is compromised. Often, the reason why cells 3 and in vivo tissue tend to be damaged is that too much power is supplied to the target cells 3. Consequently, it is essential that a DNA introducing apparatus avoids damaging the cells 3 or the like by quickly neutralizing saturation storage electric power before the cells 3 or the like are damaged.

One method for avoiding this, as was explained above, is to first introduce the desired DNA 2 to predetermined regions in the organism in advance through injection, for example. Then, with the step-up transformer 30, which is a high-impedance, high-voltage power source, voltage that has been stepped up is intermittently applied to the predetermined regions repeatedly (see FIG. 4). By applying this voltage, the biological circuit about the point of application forms an electrical free resonance circuit, and an attenuating oscillation of the molecules is induced.

Surrounding cells 3 and the introduced DNA 2 are also incorporated into the free resonance circuit, which vibrates in synchronization with the self-resonance properties of the DNA 2. That is, the DNA 2 near the cell membrane 3a is subject to based on Faraday's laws a dynamic moment in the direction against the electric field when the applied instantaneous electric field is identical to its own electric field, and in the forward direction of the electric field in the next instant when the opposite electric field is applied.

The molecular oscillation forming a maximum at this instant is constricted by the self-oscillation properties of the DNA 2. However, before the DNA 2 stops completely, it starts a molecular oscillation with a new maximum when the electric field stimulus of the next instant is applied. The molecular group making up the cell membrane 3a is also excited to oscillate through the same mechanism. Additionally, current channels depending on the potential open and close in the cell membrane 3a, thus transforming the membrane potential. The result of the continuous oscillation of the DNA 2 in accordance with its self-oscillation properties and the repeated depolarization of the cell membrane 3a is that the DNA 2 starts behaving in a manner accompanied by an accelerating motion and passes through the cell membrane 3a.

As a result, there is a marked increase in the likelihood of introducing DNA 2 into the cells 3 as compared with conventional methods of applying only direct current or the RF method, and damage to the target site and surrounding cells 3 can be reliably prevented.

It is also possible to form a magnetic field and thereby deviate the current and give rise to electron spin so as to control the resonance of molecules such as the DNA 2.

Also, generating an even stronger magnetic field loosens the double helix structure of the DNA and makes it possible to introduce molecules such as DNA 2 into the cell 3. This also enables incorporation of molecules such as DNA 2 into the genome.

There is no limitation to simple free resonance, but a variety of oscillations, such as Fourier waveform synthesis, can be applied. Thus., it is possible to cause resonance in various in vivo tissue and cells 3.

Also, by changing the resonance conditions or the shape and size of the electrodes 52 or the electrode probes 50, appropriate resonance conditions may be observed as introduction of the molecules progresses.

Moreover, because the control signal that is output by the signal control circuit 40 has a variable frequency, it can be adjusted to a period of voltage application corresponding to the DNA 2 to be introduced.

On the other hand, it is preferable that the frequency of the high voltage that is applied is 10 Hz to 1000 Hz and that the alternating voltage is applied continuously for a period of 10 seconds to 10 minutes. Then, voltage application for the period of between 10 seconds and 10 minutes is repeated.

The voltage between the pair of electrode probes 50, 50 is set to about 10,000 to about 1,000,000 volts, the impedance of the voltage applying means 12 is at least $n \times 10^{10}$ Ω, and the current flowing between the pair of electrodes 50, 50, that is, the current flowing through the cells 3 or the like, is not greater than one microampere. Consequently, the environment formed around the cell 3 has a micro current, in which almost no current flows, and a high voltage.

It should be noted that the duty ratio (t/T), that is, the ratio of the off time t to the time T, which is the time of one cycle after the switching transistor 22 is turned off to when it is next turned off, is preferably between 0.03 and 0.4.

WORKING EXAMPLE 1

GFP gene introduction and expression using a two-day old chicken hatchling and bifidobacterium was tested by repeatedly applying a high voltage of about 150,000 volts between the pair of electrode probes 50, 50.

After the GFP gene was injected into the femoral muscle of the chicken, high voltage was applied for between 30 seconds and 2 minutes. Also, high voltage was applied to the bifidobacterium in a plastic dish for between 30 and 60 seconds. It was clear at this time that the muscle cells were depolarized because twitching was observed in the hatchling's femoral muscle.

No abnormalities were found in the growth ability of the chicken and the bifidobacterium after administration of the GFP gene, and five days after introduction of the GFP gene it was confirmed that the chicken bad normal femoral muscle growth and both a uniform and high level of GFP expression.

Three days after introduction of the GFP gene, a comparison was made of the administered group (GCS) to which the molecule introducing apparatus 1 was applied and the control group (CTL) to which the molecule introducing apparatus 1 was not applied. In the GCS group, yogurt supernatants generating green fluorescence could be observed, whereas in the CTL group, fluorescence of the supernatants was not observed. Moreover, through absorption spectrum analysis it was confirmed that the GCS group expressed a unique energy absorption range spanning 340 to 400 nm, as shown in FIG. 19.

Figure 19:
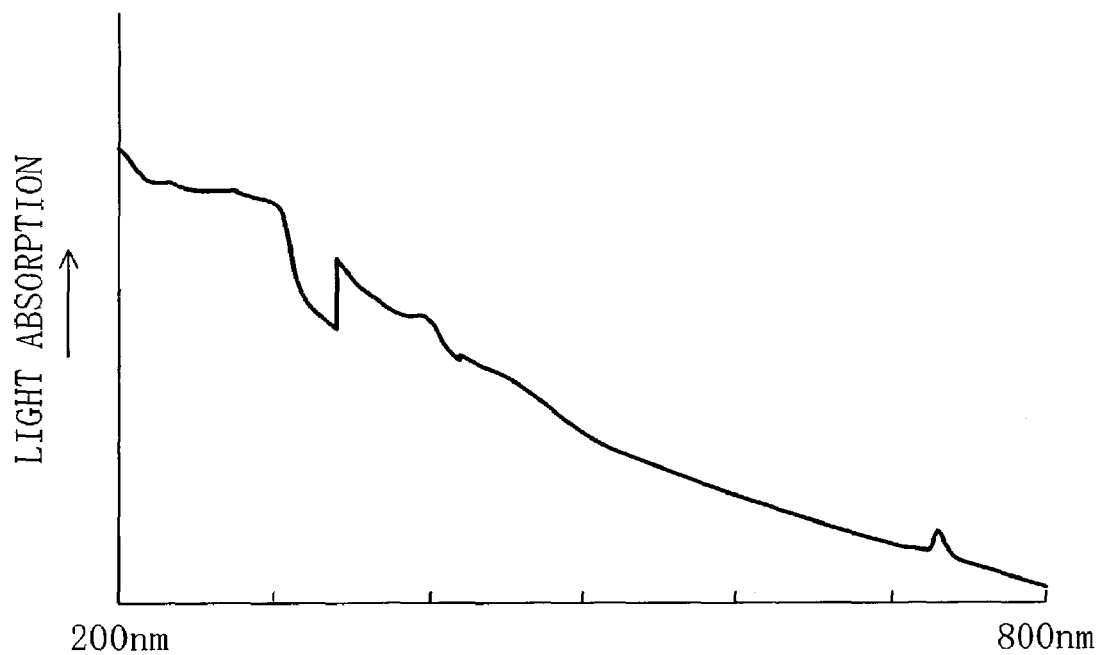
FIG. 19 is a light absorption diagram of the administered group (GCS) to which the molecule introducing apparatus is applied, and shows the test results of Working Example 1 of the first embodiment.
Figure 20:
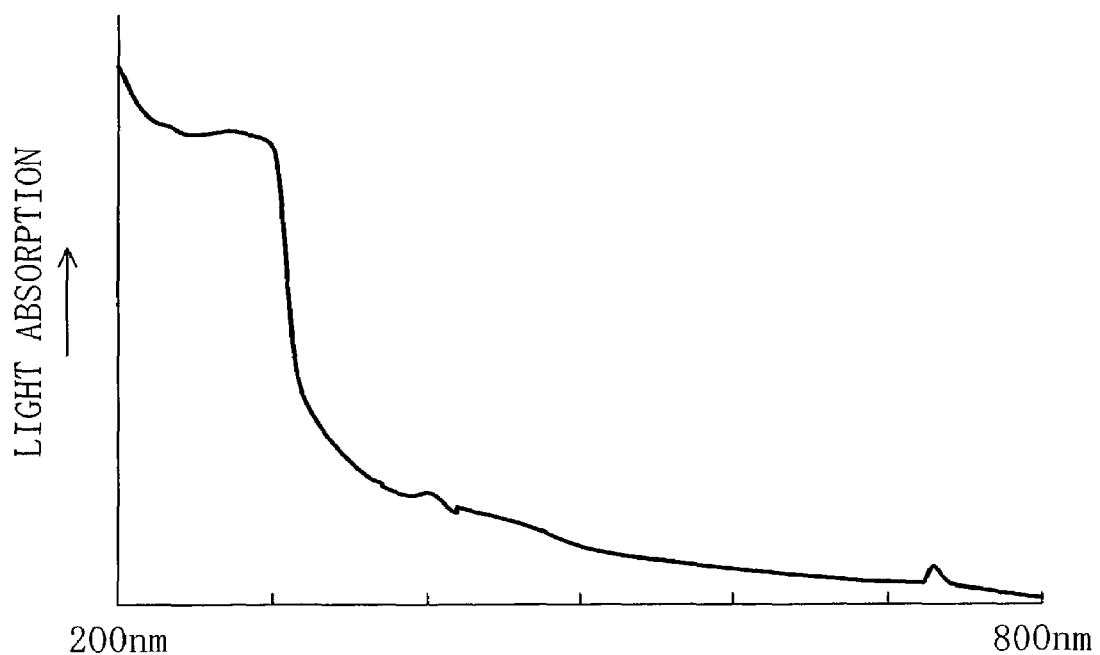
FIG. 20 is a light absorption diagram of the control group (CTL) to which the molecule introducing apparatus has not been applied, and shows the test results of Working Example 1 of the first embodiment.

FIGS. 19 and 20 demonstrate the outcome of suspension culturing the bifidobacterium of the GCS and the CTL for 72 hours in commercially sold cow's milk at 37° and then centrifugally separating them for 20 minutes at 3000 g to obtain cultured supernatants. The supernatants were introduced into a quartz cuvette and spectroscopy was performed with a spectrophotometer, at which point it was apparent that light was absorbed across 340 to 400 nm, as shown in FIG. 19, only in the GCS group.

In contrast, as shown in FIG. 20, in the CTL group a unique energy absorption range like that of the GCS group could not be confirmed.

WORKING EXAMPLE 2

Cells were deposited in a centrifugal tube and a small amount of high concentration GFP plasmid solution (20 µg) was added thereto to suspend the cells. A high voltage field was then generated by the molecule introducing apparatus 1. The frequency of the high voltage (about 150,000 volts) applied through the voltage applying means 12 was between 80 and 800 Hz, and the voltage was applied for two minutes.

In this case, GFP expression was confirmed. The GFP expression was tested twice using Hela cells and a PC12 cells, and in both instances reproducibility was demonstrated. Moreover, in this case a frequency of 160 Hz for the applied high voltage proved to be the most effective.

WORKING EXAMPLE 3

100 µg (1 µg/µl) of β-Gal expression plasmid was administered in several locations to mouse femoral muscle. Next, an instantaneous high voltage was applied to the right leg of the mouse under the following conditions, and high voltage was not applied to the left leg.

Condition 1: an instantaneous high voltage of ±150,000 volts was applied at a frequency of 160 Hz for five minutes, after which an instantaneous high voltage of 100 volts was applied at a frequency of 80 Hz for five minutes.

Condition 2: an instantaneous high voltage of ±150,000 volts was applied at a frequency of 200 Hz for five minutes, after which an instantaneous high voltage of 100 volts was applied at a frequency of 300 Hz for five minutes.

After four days, a tissue sample was taken from the femoral muscle of the mouse and subjected to X-Gal staining.

As a result, β-Gal positive cells, that is, green stained cells, were detected, thereby confirming that DNA had been introduced into the muscle tissue. The introduction of DNA was most effectively performed under Condition 2.

WORKING EXAMPLE 4

A test was performed in which anti-cyclin B1 mouse monoclonal antibodies were injected into the femoral muscle of a one-day old chicken hatchling so as to introduce protein molecules into the cells. A high voltage of ±250,000 volts centered about the potential at the ground of the specimen fixture was applied between the pair of electrode probes 50, 50 at 60 Hz for one minute to excite a resonance circuit.

At this time, the spatial distribution of the biological tissue resulted in the observation at the electrode probes 50 of the creation of spatial nitrogen plasma, spatial buzz, and various fluctuations the shape and the period of the attenuating wave on the oscilloscope for observing the electric field. These findings made it clear that by adopting the present invention, the oscillation of electrons and ionized elements distributed in the electric field, tissue, and the various types of molecules outside the apparatus themselves make a voltage waveform that follows after the instantaneous voltage. That is, the attenuating waves shown in FIGS. 4 and 5 depict the attenuating oscillation of the molecular groups, which have charge, that was observed in the free resonance circuit formed including both the inside and outside of the apparatus.

26 hours after the DNA was introduced, the femoral muscle was formalin fixated and a paraffin section was created. Then, peroxidase color reaction was developed via anti-mouse IgG secondary antibody and streptavidin-biotin bonding. This indicated that the anti-cyclin B1 antibody had been introduced and distributed to the nucleus. Therefore, it was proven that after antibody proteins move into the cell by exciting resonance they collect in the cell nucleus, which is the location of the target molecule cyclin B1.

Furthermore, FITC labeled IgG was injected into the femoral muscle of a two-day old chicken and high voltage of ±250,000 volts centered about the potential at the ground of the specimen fixture was applied between the electrode probes 50, 50 at 150 Hz for one minute to excite the resonance circuit. Five minutes later the femoral muscle was quickly frozen. A frozen section was then prepared, and as shown in FIG. 18, it was confirmed under a fluorescence microscope that there was a wide distribution of FITC fluorescence in the skeletal muscle cells.

Figure 18:
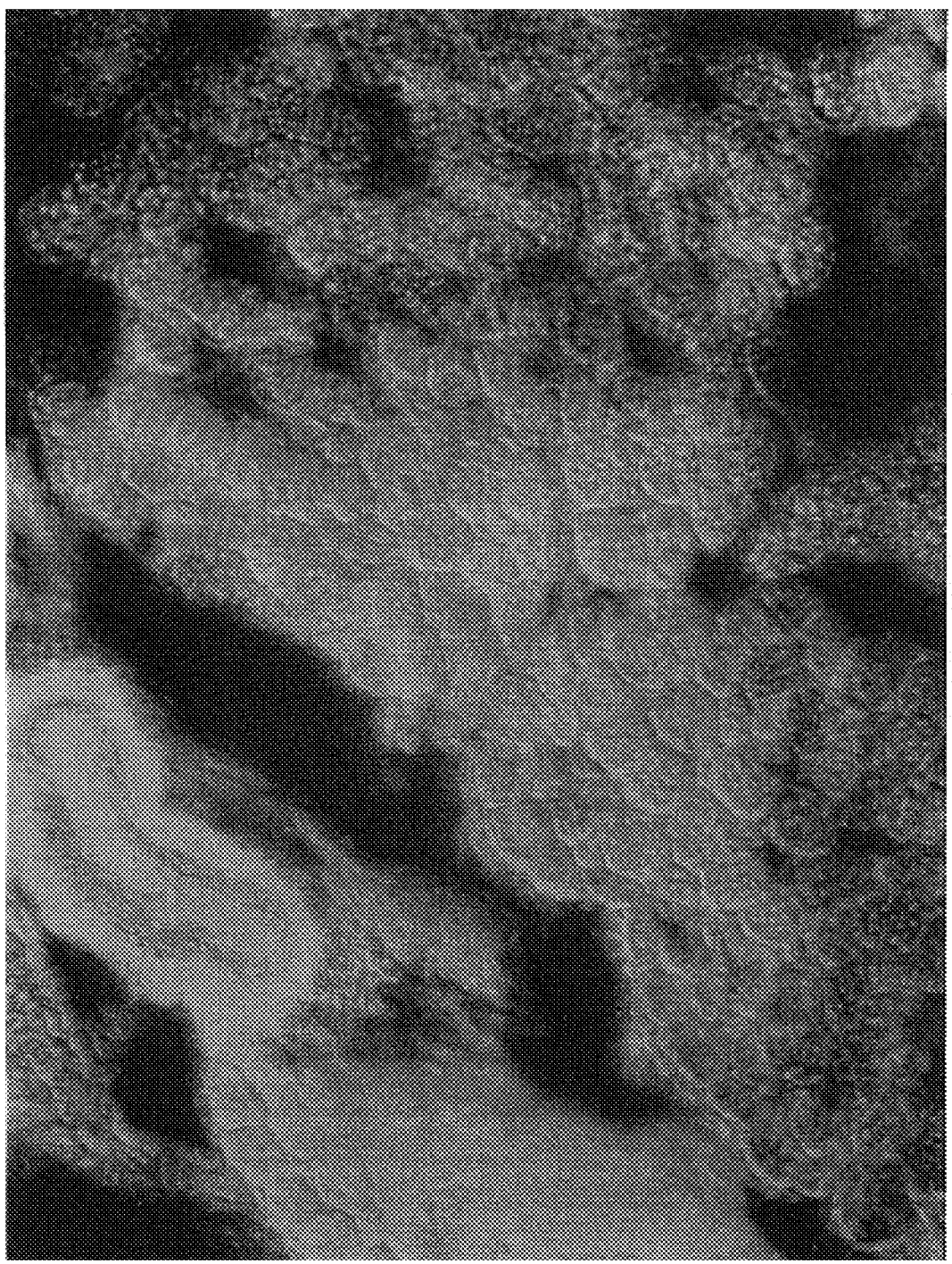
FIG. 18 is a microphotograph of chicken femoral muscle, and shows the Working Example 4 of the first embodiment.

FIG. 18 shows the skeletal muscle into which the FITC labeled antibody protein was introduced. In a Nomarski image of the cell profile superposed with the FITC fluorescence, no fluorescence can be confirmed outside the cell, that is, in the background, and green fluorescence is readily apparent in almost all muscle cell cytoplasm.

Second Embodiment

Figure 6:
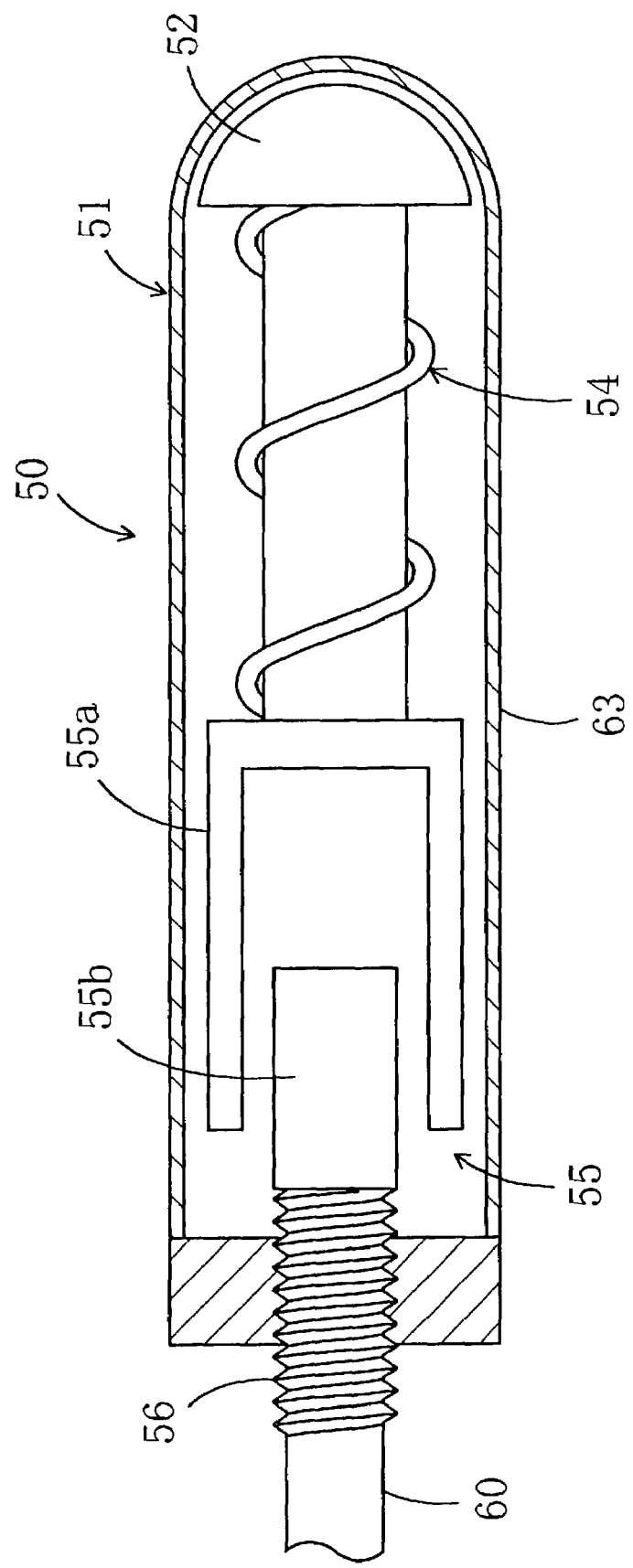
FIG. 6 is a cross-sectional view showing the electrode probes of the second embodiment.

FIG. 6 shows another embodiment of the electrode probe 50.

The electrode probe 50 of FIG. 6 has a variable capacity, and is made by providing an end electrode 52, a reactance portion 54, and a capacitor portion 55 inside the cylindrical electrode tube 51.

The end electrode 52 is accommodated and held stationary at the end portion of the electrode tube 51. One end of the reactance portion 54 is connected to the end electrode 52. The capacitor portion 55 is equivalent to the capacitor 62 of the first embodiment, and is made of a fixed electrode 55a and a movable electrode 55b. The fixed electrode 55a is connected to the reactance portion 54, whereas the movable electrode 55b is connected to the wire 60 via a screw portion 56. The screw portion 56 is fitted by screwing it into the base portion of the electrode tube 51.

Consequently, rotating the electrode tube 51 with respect to the wire 60 changes the gap between the fixed portion 55a and the movable portion 55b, and therefore changes the capacity of the capacitor portion 55. As a result, the resonance properties within the apparatus are changed. It should be noted that the electrode tube 51 is covered with a high insulation jacket 63.

A result is that an excessive voltage and a high voltage B in a residually attenuating oscillation wave of the raw amplitude can be generated. These are effective in molecule oscillation such as for the DNA 2 to be introduced.

Third Embodiment

Figure 7:
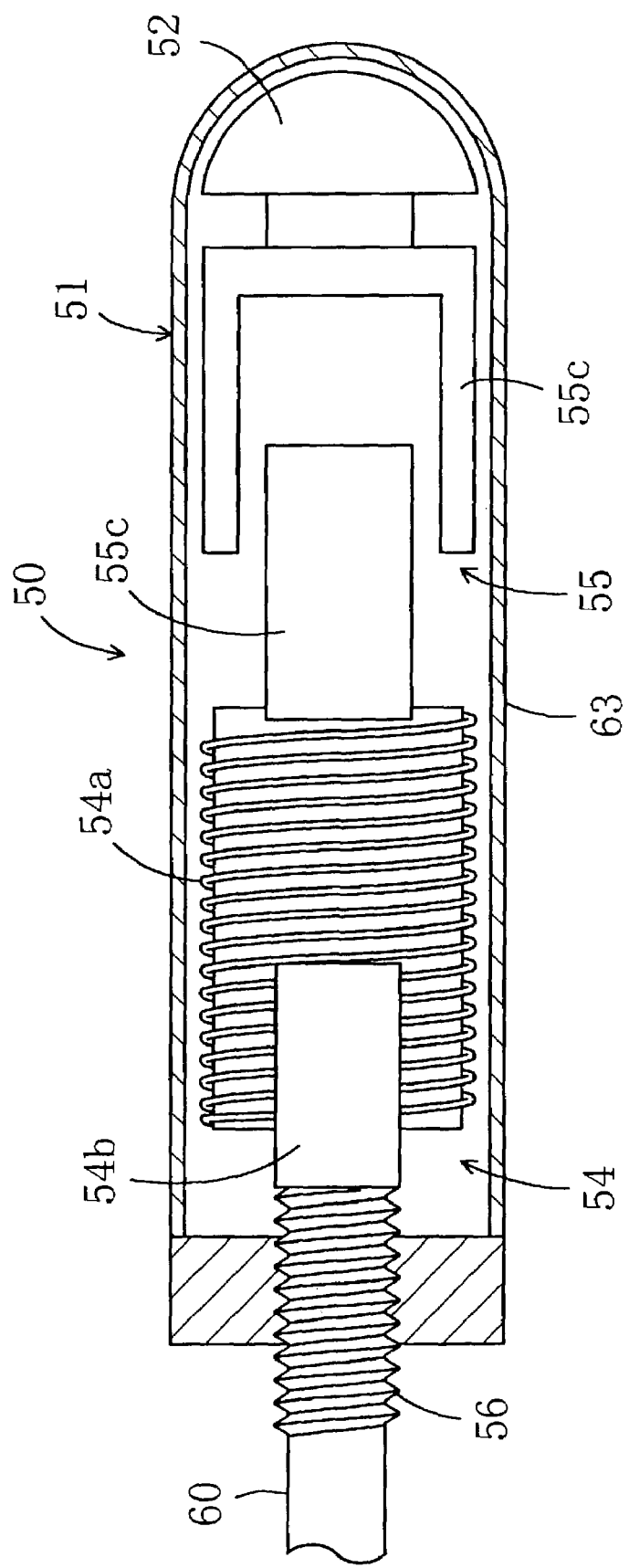
FIG. 7 is a cross-sectional view showing the electrode probes of the third embodiment.

FIG. 7 shows yet another embodiment of the electrode probe 50.

The electrode probe 50 of FIG. 7 has a variable reactance, and is made by providing an end electrode 52, a capacitor portion 55, and a reactance portion 54 inside a cylindrical electrode tube 51.

The end electrode 52 is accommodated in and held stationary by the end portion of the electrode tube 51. The capacitor portion 55 is made of two fixed electrodes 55c, 55c. One of the fixed electrodes 55c is connected to the end electrode 52, and the other fixed electrode 55c is connected to the reactance portion 54.

The reactance portion 54 is made of a coil 54a and a guide piece 54b that is connected to the coil. The coil 54a is connected to the fixed electrode 55c of the capacitor portion 55. The guide piece 54b is connected to the wire 60 via the screw portion 56. The screw portion 56 is fitted by screwing it into the base portion of the electrode tube 51.

Consequently, rotating the electrode tube 51 with respect to the wire 60 changes the spot of contact between the coil 54a and the guide piece 54b, and therefore changes the inductance of the reactance portion 54. As a result, the resonance properties within the apparatus are changed. It should be noted that the electrode tube 51 is covered with a high insulation jacket 63.

The result is that the high voltage B, which is effective in molecule oscillation such as for the DNA 2 to be introduced, can be adjusted.

Fourth Embodiment

Figure 8:
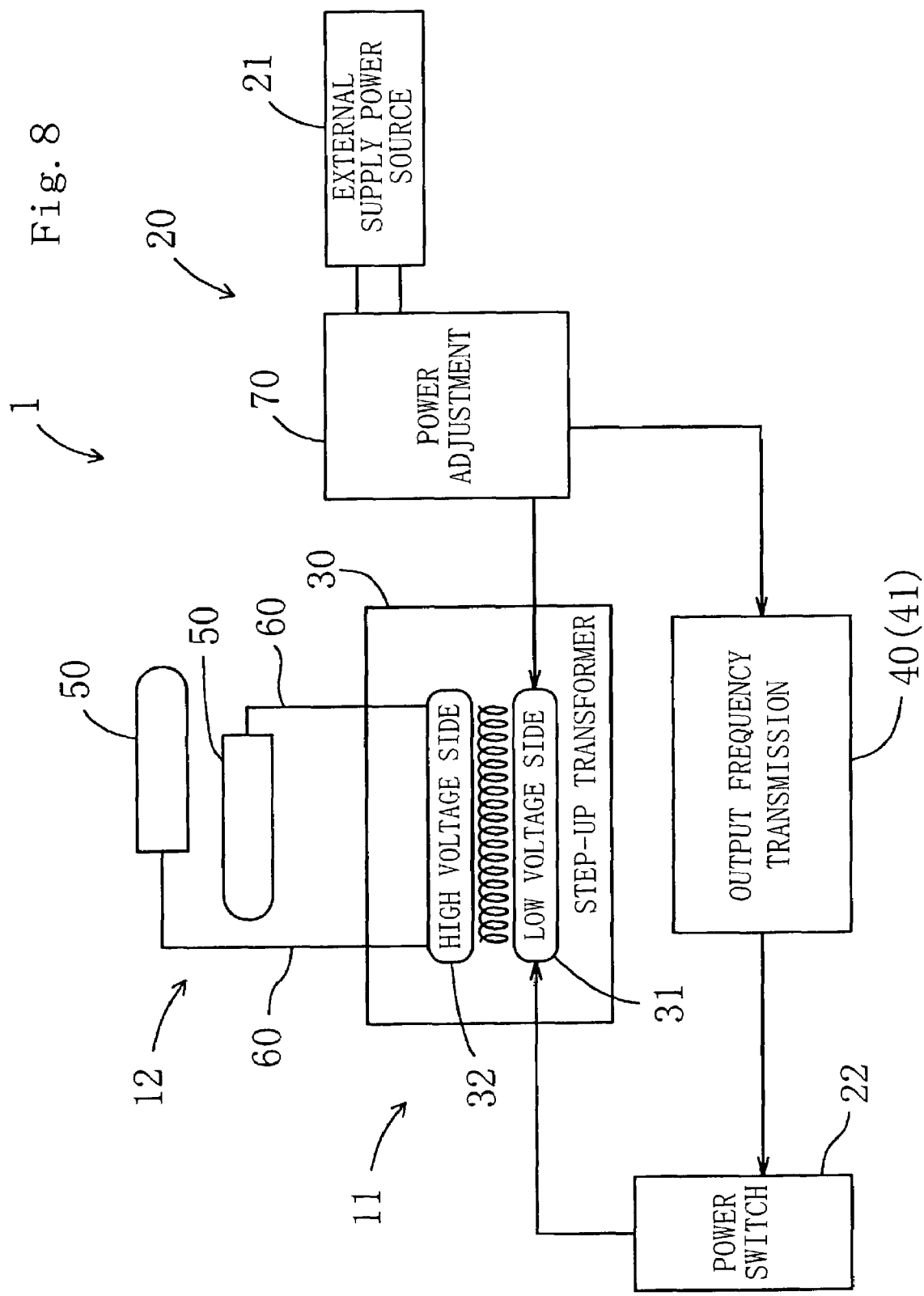
FIG. 8 is an electrical circuit diagram showing the molecule introducing apparatus of the fourth embodiment.

FIG. 8 shows another embodiment of the power supply circuit 20.

The power supply circuit 20 of FIG. 8 is provided with a power adjustment circuit 70. The power adjustment circuit 70 is configured such that it adjusts the power supplied from the power source 21 into a predetermined control power. Also, the power adjustment circuit 70 is connected to the step-up transformer 30 and the signal control circuit 40 so that it outputs the control power to the primary winding 31 of the step-up transformer 30 and the frequency generation circuit 41 of the signal control circuit 40.

Consequently, in the present embodiment the power adjustment circuit 70 creates a control power that is adopted to the DNA 2 to be introduced or the cell 3 or the like. That is, the power adjustment circuit 70 can control the current and the voltage of the power source 21.

Therefore, because the power adjustment circuit 70 has been provided, it is possible to create an instantaneous high voltage B that corresponds to the DNA 2 to be introduced, for example. As a result, the DNA 2 can be reliably passed through a membrane. More specifically, because the power adjustment circuit 70 controls the current and the voltage, it is possible to create a more precise high voltage B, which is effective in molecule oscillation such as for the DNA 2 to be introduced.

Fifth Embodiment

Figure 9:
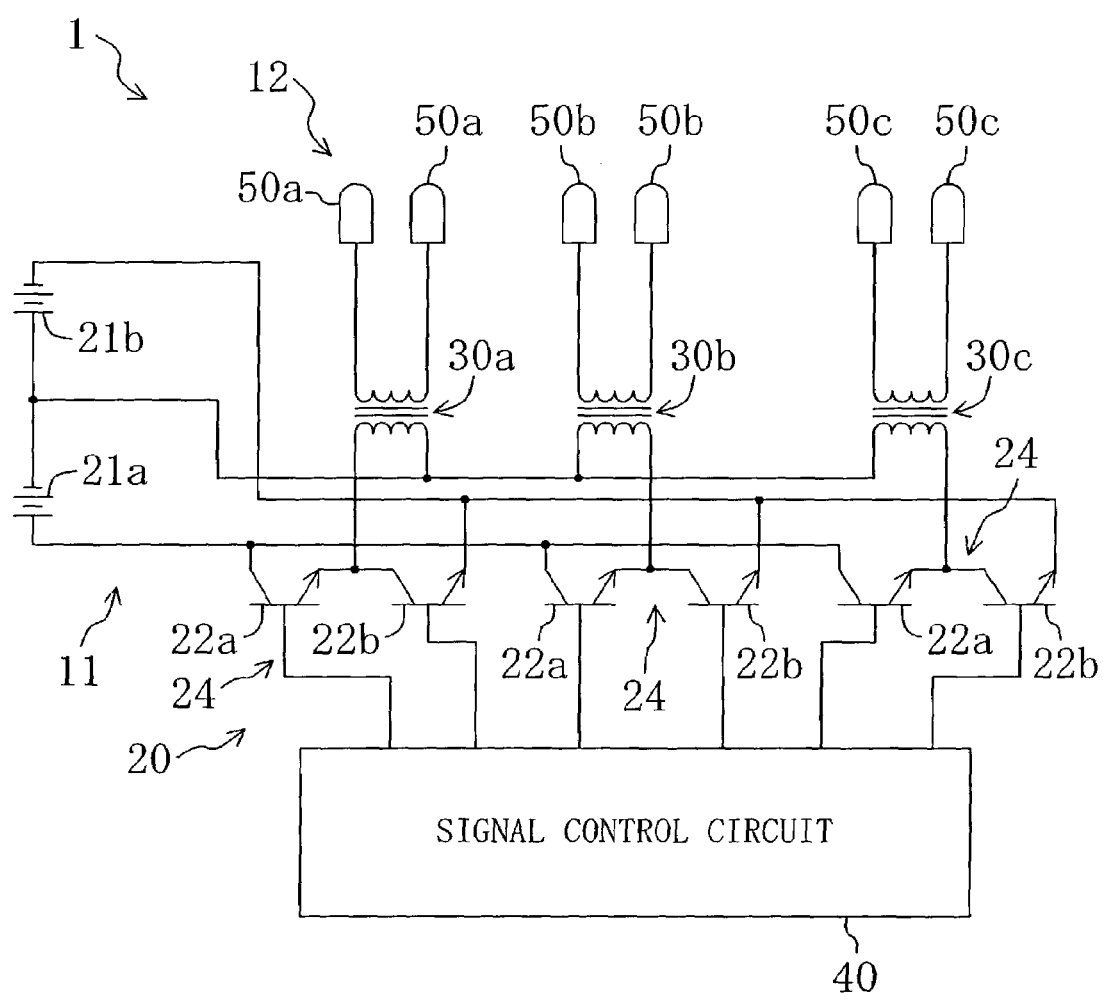
FIG. 9 is an electrical circuit diagram showing the molecule introducing apparatus of the fifth embodiment.
Figure 10:
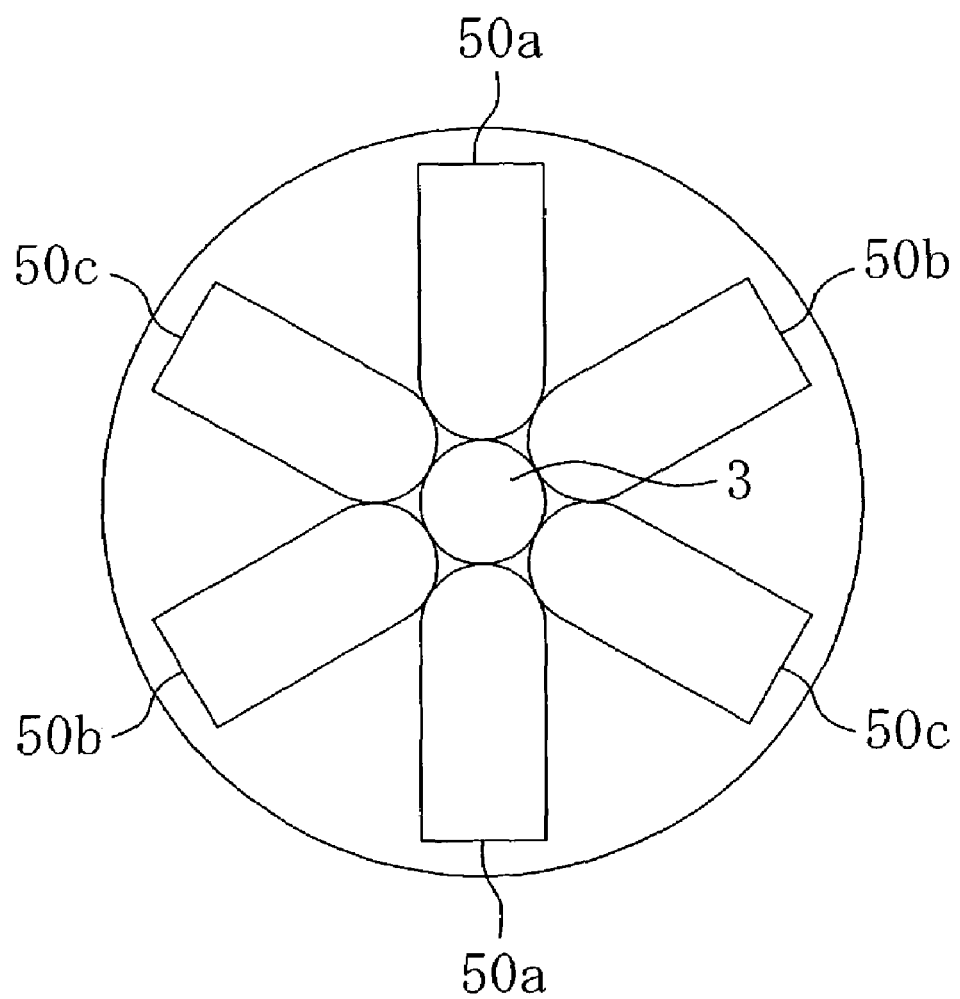
FIG. 10 is an arrangement diagram showing the arrangement of the electrode probes of the fifth embodiment.

FIGS. 9 and 10 show another embodiment of the molecule introducing apparatus 1.

This molecule introducing apparatus 1 is provided with a plurality of electrode probe pairs 50a, 50b, 50c, . . . , and more specifically is provided with three pairs of electrode probes 50a, 50b, and 50c. Also, the voltage generating means 11 is provided with three step-up transformers 30a, 30b, and 30c.

The power supply circuit 20 of the voltage generating means 11 is provided with a first power source 21a and a second power source 21b, and the positive side of the second power source 21b is connected to an end of each step-up transformer 30a, 30b, and 30c.

The voltage generating means 11 is provided with three switches 24, and each switch 24 is made of two switching transistors 22a and 22b. Collector and emitter of the two switching transistors 22a and 22b of each switch 24 are connected, and their base is connected to the signal control circuit 40.

The collector of the first switching transistor 22a of each switch 24 is connected to the plus side of the first power source 21a, and the emitter of the second switching transistor 22b of each switch 24 is connected to the minus side of the second power source 21b. Also, one end of each step-up transformer 30a, 30b, and 30c is connected to a switch 24 between the collector and the emitter of the two switching transistors 22a and 22b of that switch 24.

The signal control circuit 40 is configured such that it can output single phase alternating current-like waveforms, three phase alternating current-like waveforms, multiphase alternating current-like waveforms, and a plurality of frequencies and synthesized waveforms to each switching transistor 22a, 22b.

Consequently, when the first switching transistor 22a of each switch 24 is on, the first power source 21a lets positive current flow to the primary winding 31 of each step-up transformer 30a, 30b, and 30c, and when the first switching transistors 22a are turned off, a positive voltage burst occurs in the secondary winding 32 of each step-up transformer 30a, 30b, and 30c.

Also, when the second switching transistor 22b of each switch 24 is on, the second power source 21b delivers a negative current to the primary winding 31 of each step-up transformer 30a, 30b, and 30c, and when the second switching transistors 22b are off, a negative voltage burst occurs in secondary winding 32 of each step-up transformer 30a, 30b, and 30c.

On the other hand, the six electrode probes 50a, 50b, and 50c are arranged radially about the cells 3 into which the DNA is to be introduced, as shown in FIG. 10, and a predetermined potential difference occurs between the pairs of electrode probes 50a, 50b, and 50c.

Consequently, the voltages between the three electrode probe pairs 50a, 50b, and 50c can be made different by stepping up the voltage with each step-up transformer 30a, 30b, and 30c. Also, by the switching operation of each switching transistor 22a, 22b, . . . , voltage is applied to the DNA 2 or the like from different directions.

As a result, an instantaneous high voltage is synthesized from three instantaneous high voltage vectors and resonance can be excited that is effective for the DNA or the like. Other configurations, operations and effects are the same as those of the first embodiment.

It should be noted that although in the present embodiment three electrode probe pairs 50a, 50b, and 50c and three switches 24 were provided, it is also possible to provide a single pair of electrode probes 50a and one switch 24, which is a configuration corresponding to that of the first embodiment. Thus, it is possible to generate positive voltage bursts and negative voltage bursts.

Sixth Embodiment

Figure 11:
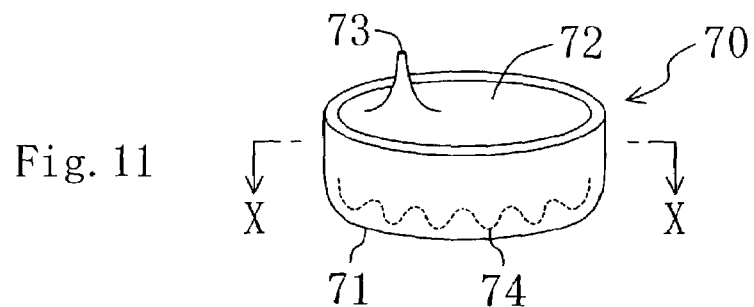
FIG. 11 is a perspective view showing the vessel for use with a molecule introducing apparatus according to the sixth embodiment.

FIG. 11 shows a vessel 70, which is an auxiliary tool for introducing DNA into cells using the molecule introducing apparatus 1.

The vessel 70 accommodates the cell solution and is formed by a material having predetermined dielectric properties. The vessel 70 is made of a bowl-shaped body 71 and a lid 72 for closing the top aperture of the body 71. Also, an air hole 73, which is a discharge aperture, is formed in the lid 72.

Examples of the material for the vessel 70 include glass, ceramic, and polymer materials (such as polyethylene, polycarbonate, or Teflon).

There is an indented portion 74 formed inside the body 71, which is configured such that a powerful electric field is generated in the indented portion 74. Moreover, the body 71 includes an insulating portion and a conducting portion so that a powerful electric field occurs in the indented portion 74.

That is, the cell solution and the DNA to be introduced into the cells are together introduced into the body 71 and the body 71 is closed off by the lid 72. At this time, air inside the body 71 is discharged from the air hole 73, and the cells in the cell solution in the body 71 concentrate in the indented portion 74.

Then, a high voltage is applied inside the vessel 70 by the electrode probes 50, 50 of the first embodiment, for example, at which time the electric field in the body 71 is concentrated at the indented portion 74, where there is a high cell density, and the electric field grows stronger. Consequently, the resonance of DNA or the like around an even greater number of cells is increased, so that the DNA 2 are introduced into the cells 3 smoothly.

The vessel 70 may also be a formed in one piece with the body 71 and the lid 72. Also, the indented portion 74 may be formed in at least a portion of the inner surface or outer surface of the body 71 or the lid 72.

MODIFIED EXAMPLES

Figure 12:
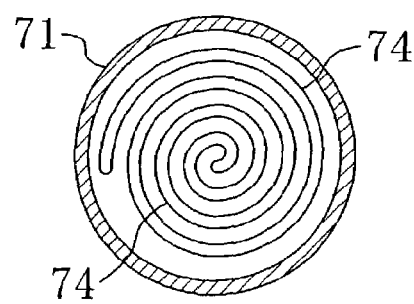
FIG. 12 is a cross-sectional view taken along the line X-X in FIG. 11 showing a modified example of the indented portion in the vessel of the sixth embodiment.
Figure 13:
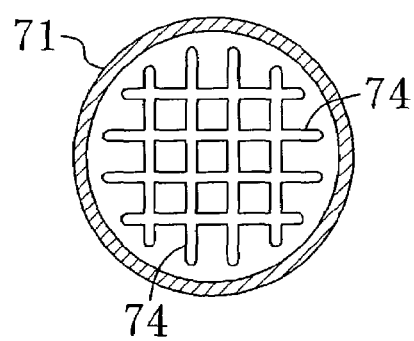
FIG. 13 is a cross-sectional view taken along the line X-X in FIG. 11 showing another modified example of the indented portion in the vessel of the sixth embodiment.
Figure 14:
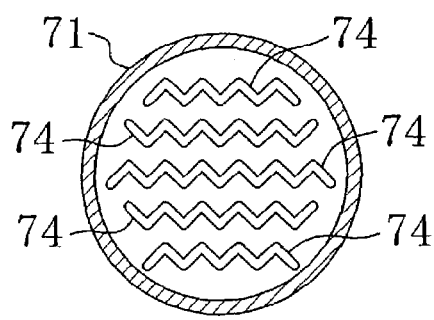
FIG. 14 is a cross-sectional view taken along the line X-X in FIG. 11 showing another modified example of the indented portion in the vessel of the sixth embodiment.

The indented portion 74 of the body 71 of the vessel 70 may also be formed in the various shapes shown in FIGS. 12 to 14.

That is, as shown in FIG. 12, the indented portion 74 may be formed in a spiral that turns from the center toward to the outside in a spirally wound fashion. The indented portion 74 can also be a plurality of concentric circles.

As shown in FIG. 13, the indented portion 74 may also be formed in a lattice.

As shown in FIG. 14, the indented portion 74 may be formed in a wavy line, and to further extend the total length of the indented portion 74, a plurality of wavy line indented portions may be provided.

Seventh Embodiment

Figure 15:
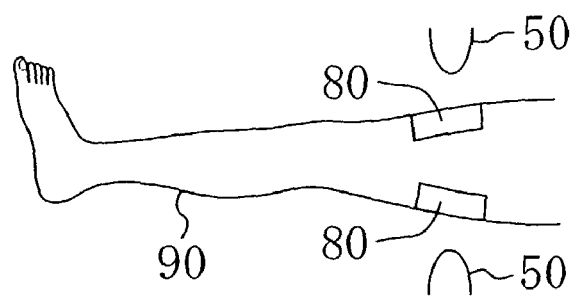
FIG. 15 is a diagram showing an auxiliary tool for use with a molecule introducing apparatus according to the seventh embodiment.

FIG. 15 shows an auxiliary tool 80 for introducing DNA into cells using the molecule introducing apparatus 1.

The auxiliary tool 80 has been configured to generate a strong electric field at predetermined regions in vivo. The auxiliary tool 80 is formed as an elastic adhesive plate with predetermined dielectric properties. Also, the auxiliary tool 80 has line-shaped conductors that are for example formed in a net-like shape, and the auxiliary tool 80 is configured to adhere to an insulating surface and to a surface of a human body 90.

Consequently, once the DNA 2 has been injected into the body, the auxiliary tool 80 is adhered to a surface of the human body 90. Then, a high voltage is applied to a predetermined region in the body by the electrode probes 50, 50 of the first embodiment, for example. At this time, the electric field is concentrated at a predetermined region by the auxiliary tool 80, making the electric field stronger, so that the resonance amplitude of the DNA 2 or the like is increased, and the DNA 2 is smoothly introduced into the cell 3.

Eighth Embodiment

Figure 16:
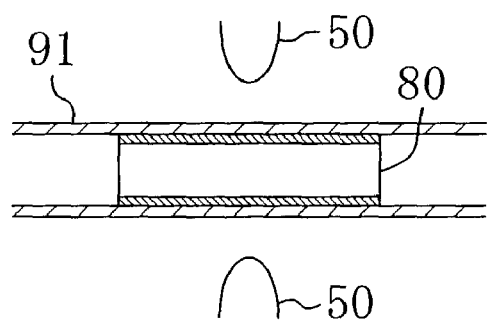
FIG. 16 is a cross-sectional view showing an auxiliary tool for use with a molecule introducing apparatus according to the eighth embodiment.

FIG. 16 shows another embodiment of the auxiliary tool 80 for introducing DNA into cells using the molecule introducing apparatus 1.

Figure 17:
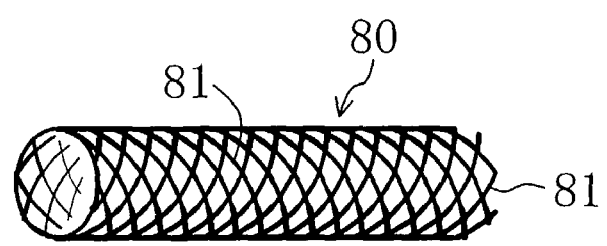
FIG. 17 is a perspective view showing the auxiliary tool of the eighth embodiment.

As shown in FIG. 17, the auxiliary tool 80 is formed in a sheath-shape with line-shaped conductors 81 formed into a net. The auxiliary tool 80 is for example introduced to and arranged inside a vein 91 via an insulating sheath.

Examples of the material for the auxiliary tool 80 include glass, ceramics, and polymer materials (such as polyethylene, polycarbonate, and Teflon).

Consequently, the auxiliary tool 80 is inserted into the vein 91 and the DNA 2 is introduced into the body. The auxiliary tool 80 and DNA 2 that has been developed onto a substrate like gel may also be made into a single unit. Then, a high voltage is applied to a predetermined region in the body by the electrode probes 50, 50 of the first embodiment, for example. At this time, the electric field is concentrated at a predetermined region by the conductors 81 of the auxiliary tool 80 to make the electric field stronger, so that the resonance amplitude of the DNA 2 or the like is increased, and the DNA 2 is smoothly introduced into the cell 3.

Other Embodiments

In the above embodiments, a step-up transformer 30, which is a transformer, is used for the voltage step-up means, but a piezoelectric element that employs a piezoelectric effect can also be used. In this case the piezoelectric element is configured so that the application of strain generates a predetermined instantaneous high voltage.

Also, in the above embodiments, the voltage applying means 12 was designed so that it applies an instantaneous high voltage, but it may also be designed so as to apply an alternating voltage or a voltage where an instantaneous high voltage is superimposed with an alternating voltage.

The voltage applying means 12 may be provided with a spark gap or a discharge tube in series or in parallel with the voltage step-up means.

The high insulation portion of the voltage applying means 12 may be a high insulation shield that is arranged in close proximity to the electrode 52.

The electrode probes 50 can be made of a conducting substance that includes metal, ceramics, or an organic substance.

By varying the applied voltage that is administered, the resonance constant or the electrode positions, it is possible to change the resonance properties and to adjust how the molecules pass the membrane.

In the above embodiments, a phantom (model organism tissue) can be adopted to make the electric field formed between the electrode probes 50, 50 visible.

Also, in the above embodiments, it is possible to employ a discharge sensor to measure the intensity of the electric field formed between the electrode probes 50, 50.

The auxiliary tool 80 is not limited to the embodiments, and it is only necessary that it is formed by an insulating portion and a conducting portion, or in other words, that it is configured to form a strong electric field at a predetermined region.

It is also possible for the molecule that is introduced to be a polynucleotide, a protein, a virus, low molecule compounds including various drugs, and a hetrocellular or a homocellular molecule.

Examples of a polynucleotide include DNA, RNA, and polynucleotide derivatives.

More specific examples of polynucleotides include CDNA, genome DNA, DNA expression vectors, and decoy nucleic acid.

Examples of proteins include analog proteins, physiologically active proteins, receptors of a physiologically active substance, antigens, monoclonal antibodies, polyclonal antibodies, antibody-like synthetic molecules, and caged molecules.

Examples of low molecule compounds including various drugs include anticancer agents, antibiotics, immunosuppresants, dyeing substances, and fluorescent substances.

Examples of substances that promote introduction of the molecule to be introduced include electrons, electron spin probe molecules, membrane potential probe molecules, optical probe molecules, anesthetics, chlorpromazines, antibiotics such as polymyxin B, cell adhesion molecules such as fibronectin, proteins, lipoproteins, peptides, and amino acids.

Organism tissue can be animal or plant tissue, and the cells 3 can be animal, plant or microbe cells or cells cloned from an animal, plant or microbe.

Examples of the above animal includes protozoa, insects, invertebrates, vertebrates, humans, and hermaphrodite organisms with reproductive organs.

Examples of microbes include viruses, bacteria, and fungi.

Examples of cells from which the organism originates include fertilized eggs, sperm, eggs, primordial germ cells, blastocysts, cell species systems, various stem cells and progenitor cells including ES cells, plant seeds, and calluses.

Examples of cloned cells include primary culture cells and following culture cells.

Also, the molecules may be prepared in a solution containing at least one of saponin, digitonin, a surfactant such as dimethyl sulfoxide, ionophores, lipids, ceramide, albumin, glycerin, gelatin, and serum, or molecules for controlling the osmotic pressure or the ion balance inside and outside the cell membrane.

The molecules may be developed into an ointment, cream, gel substrate, or fluid for injection, and administered to a body surface, adhered to a body surface, or injected into the body.

The present invention can of course also be applied to cell fusion. That is, cell fusion is ordinarily carried out by fusing cells using polyethylene glycol. Also, for cells with a cell wall, this is performed after protoplastization. However, polyethylene glycol is cytotoxic, which complicates increasing the fusion efficiency. Accordingly, adopting the molecule introducing apparatus of the present invention to oscillate the cell membranes results in cell fusion without the use of polyethylene glycol.

Also, the present invention can of course also be applied to breeding and genetically modifying plants. Genetically modified plants are created through the following process.

First, DNA is introduced into cultured plant cells using an adenovirus or particle gun. Next, the cells into which the DNA is introduced are selected and those cell are cultured and separated into individual plants.

However, genetically modifying plants requires that a cultured cell is established and that a method for the tissue culture of cells into individual plants is established, as mentioned above, and therefore genetic alteration is not possible for all plants. Aside from plants such as tobacco and rice, which can be genetically manipulated with relative ease, genetic modification at the current moment poses many problems.

Accordingly, the molecule introducing apparatus of the present invention was adopted and DNA was introduced into the entire seed using a gene synthesizer. As a result, the tissue culturing process can be omitted, and a novel method for the genetic alteration of plants that is non-selective of the plant type is possible.

Ordinarily, the introduction of DNA into a plant is performed using an Agrobacterium vector, a particle gun, or electroporation. However, unlike animal cells, plant cells have a cell wall. This lowers the effectiveness of DNA introduction into plant cells and necessitates protoplastization, through which the cell well is dissolved, and the induction of calluses. Because the present invention causes oscillations in cell walls and cell membranes alike, it is possible to introduce DNA without performing protoplastization or inducing calluses. Furthermore, because the present invention causes little damage to cells, it provides a DNA introduction method through which DNA is very effectively introduced into plant cells.

INDUSTRIAL APPLICABILITY

As set forth above, the molecule introducing apparatus and the molecule introducing method according to the present invention are useful in introducing molecules into cells, and can find application in gene therapy, regenerative therapy, introducing drugs into target tissue and target cells, breeding plants and animals, transgenic engineering, creating genetically altered organisms, cell fusion, and synthesizing artificial substances, for example.

The invention claimed is:

1. A molecule introducing apparatus, comprising:
   a voltage applying means, including:
   a plurality of electrodes placed close to each other in a gas, wherein the electrodes are adapted to generate an electric field around biological tissues or cells and exogenous molecules arranged outside the biological tissues or the cells via an insulation portion and wherein, from a single spike voltage, the electrodes are adapted to generate a non-porating electric field positioned around constituent molecules constituting a biological tissue or a cell for exciting a free resonance vibration of the constituent molecules and exogenous molecules arranged outside the biological tissue or the cell so as to cause reverberation between the constituent molecules and the exogenous molecules, the resonance vibration and the reverberation introducing the exogenous molecules into the biological tissue through a membrane of the biological tissue or into the cell through a membrane of the cell without poration of the membrane of the biological tissue or the cell; and a voltage generating means, including:
  a power supply means for supplying power;
  a voltage step-up means, which steps up voltage supplied from the power supply means and then supplies the voltage to the voltage applying means;
  a switching means, which blocks/allows the supply of power from the power supply means to the voltage set-up means to generate the single spike voltage to be supplied from the voltage step-up means to the voltage applying means; and
  a switching control means for controlling the switching of the switching means, wherein the single spike voltage consists of a single pulse.

2. The molecule introducing apparatus according to claim 1, wherein the power supply means comprises:
  a DC power source; and
  a power adjustment circuit for adjusting the voltage to be supplied from the power source to the voltage step-up means, and
  the switching control means is configured so that it outputs a control signal with a variable frequency to control the driving of the switching means.

3. The molecule introducing apparatus according to claim 1, wherein a frequency of the spike voltage generated by the switching means to 10 Hz to 1000 Hz.

4. The molecule introducing apparatus according to claim 1, wherein the voltage step-up means is a transformer.

5. The molecule introducing apparatus according to claim 1, wherein the voltage applying means is provided with a plurality of electrodes and insulation portions, and is configured such that the electrodes generate an electric field around the biological tissues or the cells and the exogenous molecules arranged outside the biological tissues or the cells via at least one of the insulation portions.

6. The molecule introducing apparatus according to claim 1, wherein the voltage applying means comprises:
  an electrode portion;
  a capacitor portion; and
  a reactance portion, wherein either the capacitor portion or the reactance portion is made variable.

7. The molecule introducing apparatus according to claim 1, wherein the insulating portion of the voltage applying means is any one of an insulating shield arranged in close proximity to the electrodes, an insulation jacket that covers the electrodes, or an insulating shield arranged in close proximity to a periphery of the biological tissues or the cells.

8. The molecule introducing apparatus according to claim 5, wherein the insulation portion of the voltage applying means is any one of an insulating shield arranged in close proximity to the electrodes, an insulation jacket that covers the electrodes, or an insulating shield arranged in close proximity to a periphery of the biological tissues or the cells.

9. The molecule introducing apparatus of claim 1 further comprising an auxiliary tool which comprises:
  a vessel body which has predetermined dielectric properties and in which a cell is housed, the cell being positioned between electrodes facing each other,
  wherein the vessel body has an indented portion which concentrates an electric field on at least a portion of the vessel body.

10. The molecule introducing apparatus of claim 1 further comprising an auxiliary tool which has predetermined dielectric properties and which is arranged at a predetermined region of an organism, and which concentrates an electric field on the predetermined region by applying a spike voltage to the predetermined region through electrodes directed to the predetermined region and facing each other.

11. A molecule introducing method, comprising:
  generating a single spike voltage consisting of a single pulse using a plurality of electrodes placed close to each other in a gas; and
  creating, from the single spike voltage, a non-porating electric field positioned around constituent molecules constituting a biological tissue or a cell for exciting a free resonance vibration of the constituent molecules and exogenous molecules arranged outside the biological tissue or the cell so as to cause reverberation between the constituent molecules and the exogenous molecules, the resonance vibration and the reverberation introducing the exogenous molecules into the biological tissue through a membrane of the biological tissue or into the cell through a membrane of the cell without poration of the membrane of the biological tissue or the cell.

* * * * *